(12) United States Patent
Gray et al.

(10) Patent No.: US 11,724,058 B2
(45) Date of Patent: Aug. 15, 2023

(54) FLUID TRAP FOR A RESPIRATORY THERAPY SYSTEM

(71) Applicant: Fisher & Paykel Healthcare Limited, Auckland (NZ)

(72) Inventors: Nathan Lee Gray, Auckland (NZ); Telge Nishan Chaturanga Peiris, Auckland (NZ); Paul Joseph Moody, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 811 days.

(21) Appl. No.: 16/487,343

(22) PCT Filed: Feb. 21, 2018

(86) PCT No.: PCT/NZ2018/050015
§ 371 (c)(1),
(2) Date: Aug. 20, 2019

(87) PCT Pub. No.: WO2018/156033
PCT Pub. Date: Aug. 30, 2018

(65) Prior Publication Data
US 2020/0023154 A1  Jan. 23, 2020

Related U.S. Application Data

(60) Provisional application No. 62/507,065, filed on May 16, 2017, provisional application No. 62/461,708, filed on Feb. 21, 2017.

(51) Int. Cl.
*A61M 16/08* (2006.01)
*A61M 16/20* (2006.01)

(52) U.S. Cl.
CPC .... *A61M 16/0808* (2013.01); *A61M 16/0816* (2013.01); *A61M 16/206* (2014.02)

(58) Field of Classification Search
CPC .......... A61J 1/10; A61J 1/2037; A61M 11/00; A61M 11/003; A61M 11/005;
(Continued)

(56) References Cited

U.S. PATENT DOCUMENTS 3,356,100 A * 12/1967 Seeler ................. A61M 16/208
                                                137/854
4,268,460 A *  5/1981 Boiarski ............... A61M 16/14
                                                261/78.2
(Continued)

FOREIGN PATENT DOCUMENTS

GB         1456570      11/1976
GB         2 272 745    11/1992
(Continued)

OTHER PUBLICATIONS

Patent Cooperation Treaty, Written Opinion and International Search Report, Application No. PCT/NZ2018/050015, dated May 18, 2018, in 9 pages.

*Primary Examiner* — Annette Dixon
(74) *Attorney, Agent, or Firm* — Knobbe, Martens, Olson & Bear, LLP

(57) ABSTRACT

Disclosed is a fluid trap for use with, or comprising part of, a respiratory therapy system, d particular comprising part of, or configured to be connected to, a breathing limb, such as an expiratory limb, of a respiratory therapy system. The fluid trap comprises a container configured to contain fluid received from an inlet; a closure, the closure and container being configured to be removeably mounted together to close the container; and a valve configured to be removeably mounted on at least one of the container and the closure, and configured to be in a closed condition which prevents fluid from flowing through the inlet when the closure is not mounted on the container, the valve being further configured
(Continued)

to be in an open position which allows fluid from the inlet into the container when the closure is mounted on the container.

19 Claims, 19 Drawing Sheets

(58) Field of Classification Search
CPC .. A61M 11/02; A61M 15/00; A61M 15/0013; A61M 15/0018; A61M 16/0009; A61M 16/0051; A61M 16/021; A61M 16/0452; A61M 16/0465; A61M 16/0472; A61M 16/0475; A61M 16/0479; A61M 16/0484; A61M 16/0486; A61M 16/0493; A61M 16/0808; A61M 16/0816; A61M 16/0833; A61M 16/0858; A61M 16/0875; A61M 16/1045; A61M 16/1055; A61M 16/106; A61M 16/1065; A61M 16/1075; A61M 16/14; A61M 16/16; A61M 16/167; A61M 16/20; A61M 16/208; A61M 2016/0021; A61M 2016/0027; A61M 2025/004; A61M 2025/0073; A61M 2039/2433; A61M 2039/268; A61M 2205/7527; A61M 2205/7536; A61M 25/0068; A61M 25/007; A61M 25/0082; A61M 25/04; A61M 25/0606; A61M 25/0668; A61M 39/26; B01D 45/02; B82Y 10/00; F16K 21/04; F16K 3/029; F16K 3/04; F16L 37/30; F16L 37/32; F16L 37/38; F16T 1/20; G01L 9/0072; H01L 51/0004; H01L 51/0038; H01L 51/0046; H01L 51/0048; H01L 51/0097; H01L 51/4206; H01L 51/424; H01L 51/4253; H01L 51/447; Y02E 10/549; Y02P 70/50; Y10S 128/911; Y10S 128/912; Y10S 55/35; Y10T 137/3003; Y10T 137/7668

See application file for complete search history.

(56) References Cited

U.S. PATENT DOCUMENTS

| 4,417,574 | A | * | 11/1983 | Talonn | A61M 16/0808 |
| | | | | | 96/219 |
| 4,457,305 | A | * | 7/1984 | Shanks | A61M 16/0808 |
| | | | | | 55/DIG. 35 |
| 4,951,661 | A | * | 8/1990 | Sladek | A61M 16/0808 |
| | | | | | 128/205.24 |
| 5,168,868 | A | * | 12/1992 | Hicks | A61M 16/0808 |
| | | | | | 128/205.12 |
| 5,388,571 | A | * | 2/1995 | Roberts | A61M 16/16 |
| | | | | | 128/205.12 |
| 7,383,852 | B2 | * | 6/2008 | Pittaway | B01D 45/02 |
| | | | | | 137/454.6 |
| 2010/0252035 | A1 | | 10/2010 | Chang | |
| 2010/0258189 | A1 | | 10/2010 | Curran | |
| 2012/0017907 | A1 | | 1/2012 | Hsiao | |
| 2012/0266888 | A1 | | 10/2012 | Dwyer et al. | |
| 2015/0335852 | A1 | | 11/2015 | Miller | |

FOREIGN PATENT DOCUMENTS

| GB | 2465253 | 5/2010 |
| WO | WO 2003/047674 | 6/2003 |

* cited by examiner

FLUID TRAP FOR A RESPIRATORY THERAPY SYSTEM

This application claims priority from U.S. provisional application 62/461,708 filed Feb. 21, 2017 and U.S. 62/507,065 filed May 16, 2017, the entire contents of both of which are hereby incorporated by reference.

BACKGROUND

Field of the Disclosure

The present disclosure generally relates to a fluid trap for use with, or comprising part of, a respiratory therapy system, and in particular comprising part of, or configured to be connected to, a breathing limb, such as an expiratory limb, of a respiratory therapy system.

Description of the Related Art

A respiratory therapy system typically delivers heated and humidified gases for various medical procedures, including respiratory treatment, laparoscopy and the like. Such a system can be configured to control temperature, humidity and flow rates. Respiratory humidification can also be used in respiratory therapy systems.

A respiratory therapy system is typically used for the treatment of respiratory conditions such as, for example, obstructive sleep apnea (OSA) or chronic obstructive pulmonary disease (COPD). This disclosure relates to any respiratory therapy system, for treatment of any respiratory condition.

A respiratory therapy system may include an inspiratory flow path along which breathing gas is delivered from a gas source to the patient, and an expiratory flow path along which expiratory gas flows from the patient. The inspiratory and expiratory flow paths may be the same, but are typically different. Examples of a gas source include a source of pressurised gas, or a ventilator, or a flow or pressure generator comprising a blower (typically comprising an impellor and a motor). This flow path is typically referred to as the breathing circuit which comprises one or more breathing limbs. The components of the breathing limb comprising the inspiratory part of the breathing circuit are known as the inspiratory limb of the system, and typically comprise one or more sections of inspiratory gas delivery conduit and one or more connectors that connect the section(s) of conduit between the source of breathable gas and a patient interface that delivers the breathable gas to the patient. A humidifier may be provided between the source of gas and the breathing circuit to humidify the breathable gas.

Expired gases from the patient flow from the patient interface along an expiratory flow path or are vented to atmosphere. The components of the breathing limb comprising the expiratory part of the breathing circuit are known as the expiratory limb, also comprising a combination of one or more sections of expiratory conduit and connectors.

The breathing circuit can therefore deliver heated and humidified air to the patients. To prevent "rainout" (the formation of condensation in the breathing circuit), the inspiratory conduit may be insulated and/or heated to at least minimise the temperature drop of the breathable gas flowing along the inspiratory limb. However, all or part of the or each breathing limb may not be heated. For example, the expiratory limb of the breathing circuit may not be heated, as there is no benefit to the patient and the redelivery of humidified air to the ventilator can cause damage. Accordingly, cooling water vapour in the gases can condense in the expiratory limb. Such condensate in the expiratory limb can run into the ventilator causing damage to the ventilator.

A fluid trap may be used to collect fluid formed or introduced into the breathing circuit, and typically in the expiratory limb. That fluid typically includes condensate from the expired gas, and any other fluid from the patient, such as mucus or saliva for example. Such a fluid trap can be useful when there is artificial ventilation being provided to a very sick patient. These patients are generally intubated and the respiratory therapy system includes both an inspiratory line and an expiratory line.

Fluid traps may be located so as to intersect breathable gas conduits and have inlet/outlet ports which connect the conduits to the fluid trap at an angle from the vertical axis of the fluid trap container, for example, the inlet/outlet ports are in a 'V' configuration with respect to the fluid trap and each other. This can be undesirable because, when the fluid trap is in use around a patient bedside, it is difficult to keep the trap level and therefore it is difficult to keep the conduits draining to the fluid trap properly. Instead, the fluid trap is frequently askew, limiting the amount of fluid that it can hold without leaking, and shortening the allowable time between emptying.

SUMMARY OF THE DISCLOSURE

In accordance with aspects of the disclosure, a re-useable fluid trap differs from a disposable fluid trap in that a re-useable fluid trap should be reprocessable, that is, capable of undergoing cleaning processes that can include (1) cleaning of visible contaminants and debris (2) disinfection such as pasteurisation, heat and chemical treatments, and (3) sterilisation by processes such as gas-, chemical- and heat-sterilisation, e.g. autoclaving. Re-useable and disposable water traps can be used in respiratory humidification systems. Re-useable water traps are often used in developing nations, for cost reasons, or for environmental reasons. Additionally, it is desirable that the trap is able to be relatively easily re-assembled after emptying of the fluid trap and, particularly in the case of reusable water traps, after reprocessing. As such, a simple device that uses as few parts as possible may be desirable. Additionally, it may be desirable to prevent or resist (re)assembly of the reusable fluid trap in an incomplete state. By way of example, if the reusable fluid trap was to be reassembled incorrectly the breathing circuit may leak, causing a possible drop in treatment pressure or an infection risk. Additionally, it can be desirable for the fluid trap to have a small compressible volume, as the increase in the compressible volume provided by the fluid trap may result in delay of the pressure waveform reaching the ventilator, throwing off breathing circuit performance.

It is an object of the present disclosure to provide a fluid trap, which in some embodiments may be reusable and in some embodiments disposable, for a respiratory therapy system which solves or at least alleviates one or more of the above problems, and/or that will at least provide the public or the medical profession with a useful choice.

Accordingly in one aspect the invention may broadly be said to consist of a fluid trap for a breathing limb of a respiratory therapy system, comprising:

at least one inlet configured to be connected to the breathing limb to receive fluid from the breathing limb;
a container configured to contain fluid received from the inlet;

a closure, the closure and container being configured to be removeably mounted together to close the container; and a valve configured to be removeably mounted on at least one of the container and the closure, and configured to be in a closed condition which prevents fluid from flowing through the inlet when the closure is not mounted on the container, the valve being further configured to be in an open position which allows fluid from the inlet into the container when the closure is mounted on the container.

The fluid trap could be reusable, in that the fluid trap could be suitable for multiple patient use and/or may be reprocessable.

Alternatively, the fluid trap could be disposable that is, for single use only.

The breathing limb could be an expiratory limb, the trap being provided at a position along the length of the expiratory limb.

The fluid trap may be provided at any desired position along a breathing limb of the system.

In one example, the trap may be positioned at or adjacent to a catheter mount of a breathing limb of the system. The catheter mount is the apparatus that connects an inspiratory tube of the system to an endotracheal tube. The catheter mount generally has a connector comprising a wye piece connector or an elbow connector which is typically unheated and which can therefore result in condensate forming near the patient. A fluid trap in accordance with the present disclosure could be configured to be mounted at or adjacent the catheter mount. In such an example, the trap may be of relatively small volume. The relatively small volume is preferably small enough such that the delivered waveform of the flow or pressure of the breathable gas delivered to the user is not significantly or adversely affected.

The valve may be formed from a resiliently deformable material. In some embodiments the valve is configured such that resilient deformation of the valve moves the valve from the closed condition to the open condition when the container and closure are mounted together. The deformation may be of a part of the valve which seals against the inlet, or may be of another part of the valve, deformation of that other part of the valve moving the part of the valve which seals against the inlet.

In some embodiments the valve is configured to be mounted on one of the container and the closure so as to be located between the closure and the container when the closure and the container are mounted together.

In some embodiments the valve is a mushroom valve comprising a peripheral skirt and a central valve stem. The peripheral skirt may form a seal between the closure and the container when the closure and the container are mounted together. The central valve stem may form a seal with the inlet when the valve is in the closed condition. The valve may be configured so as to be resiliently deformable to move the valve stem relative to the peripheral skirt as the closure and the container are mounted together.

The valve may comprise, in transverse cross section, at least one lower projection which engages the container, at least one upper projection that engages the closure, relative axial movement between the closure and container causing relative movement between the upper and lower projection which deforms the valve into the open condition. The valve may comprise a substantially 'W' shaped transverse cross section having, in transverse cross section, a pair of upper projections and a pair of lower projections and a central valve stem. The container and valve may be configured such that during assembly of the fluid trap, the container pushes against the lower parts of the 'W' to push the valve into the closure and/or to deform the valve such that the upper part of the 'W' sealing engages the closure.

In some embodiments, the valve may comprise a central projection that is sealingly engageable with the inlet, the sealing engagement being dependent on whether the closure and the container are mounted together. At least one of the container and the closure comprise a drive formation configured to engage the valve to deform or move the valve as the closure and the container are mounted together, such that the valve is in the open condition when the closure and container are mounted together. The valve may comprise a 'U' or 'V' shaped transverse cross section.

The valve may comprise one or more cut-outs or recesses configured to reduce the weight and/or to improve the flexibility of the valve. The cut-outs or recesses are also configured to allow fluid flow or fluid transfer from the closure to the container. The cut-outs are formed in portions of the valve, and are large enough to provide no or low impedance to flow between an inlet and the container, while allowing the valve to maintain a biasing force such that the valve rests against a valve seat when the container and closure are disengaged.

In an embodiment the cut-outs extend radially outward from the stem of the valve. The cut-outs may be triangular or trapezoidal or rectangular in shape. In an alternative embodiment the cut-outs may extend concentrically partially around the body of the valve. In this alternative embodiment the cut-outs may be circular in shape or may be concentric rings that extend around the body of the valve. The concentric cut-outs may be centred around the valve stem. The cut-outs are formed by any suitable manufacturing process such as cutting or moulding.

In some embodiments the closure, container and valve are configured such that the container and the closure cannot be mounted together unless the valve is present. The valve may therefore comprise one or more mounting formations configured to engage with the closure, and one or more mounting formations configured to engage with the container. In some embodiments the mounting formations of the valve engage with the container and/or the closure with a frictional fit. The or each mounting formation may therefore comprise a mounting surface that engages with the closure and/or container. In other embodiments, the mounting formations may comprise a projection or other mechanical structure configured to engage with a corresponding mechanical structure on the closure and/or container. The or each mounting formation may therefore comprise a screw thread or bayonet type connector.

Preferably the valve is configured to perform at least a first function of providing a valve that opens or closes the inlet and a second function of providing a fluid seal between the container and the closure. The valve may comprise a biasing means or spring to bias the valve to the open condition, when the container and closure are in the fully assembled condition.

The valve may comprise a sealing formation which sealingly engages with the closure and/or container. The sealing formation may comprise at least one o-ring or half o-ring formation configured to sealingly engage the container and/or the closure. The container and/or closure may comprise a sealing formation configured to sealingly engage with the valve. The valve assists in retaining the closure and container in an engaged or locked arrangement. The valve provides a friction fit to assist in engaging the closure to the container. In some embodiments, the sealing formation and the mounting formation may be the same structure.

In some embodiments the container and the closure may be mounted together using a push-rotate fit, whereby the closure and the container are pushed together in a direction along the longitudinal axis of the container/closure, and simultaneously rotated relative to one another about the longitudinal axis of the container/closure.

In some embodiments at least one of the container and the closure comprise a guiding formation configured to guide the other of the container and the closure as the container and closure are pushed and rotated together. In some embodiments the guiding formation comprises a ramped portion on at least one of the container and closure, inclined relative to the longitudinal axis of the fluid trap, and configured to guide the container and the closure together in a longitudinal direction along the longitudinal axis. The guiding formation may alternatively or additionally be configured to guide the container and the closure together in a rotational direction about the longitudinal axis.

At least one of the container and closure may comprise one or more flanges that protrude outwardly from the container or closure, the or each flange being configured to engage with the guiding formation and move along the guiding formation as the container and closure are urged together into a closed position. A plurality of flanges may be provided on either the container or closure. The or each flange may be disposed around the periphery of the container or closure. The or each flange may extend generally radially outwardly from the outer periphery or circumference of the container of closure. The or each flange may rest on the guiding formations when the container and closure are in a closed position, and may rest against the end stop(s).

In one embodiment a plurality of flanges are provided on the container periphery and the guiding formations are provided on the downwardly extending skirt of the closure.

In some embodiments the or each guiding formation comprises an end stop configured to prevent or resist further movement of the container relative to the closure, when the closure is fully mounted on the container. The or each flange may include a bump or protrusion at one end that can engage a slot in the guiding formation, adjacent the end stop.

In some embodiments a security formation is configured to provide at least one of an audible and tactile confirmation that the container and the closure are fully mounted together. The bump/protrusion of the or each flange may engage a slot in the end stop to create an audible and tactile confirmation of engagement between the closure and container in the closed position.

In some embodiments one of the container and closure comprises a peripheral lip configured to be positioned adjacent a longitudinally extending peripheral skirt provided on the other of the container and the closure, the lip comprising at least one radially inwardly or outwardly directed flange configured to be received in a corresponding recessed portion of the skirt, relative rotation between the container and the closure causing the flange to overlap with a non-recessed portion of the skirt, the overlap resisting removal of the closure from the container in a longitudinal direction. The or each flange can interact with the guiding formations above.

A plurality of flanges may be provided, and the circumferential length of the or each flange may be between half the distance between two guiding formations and a length equivalent to the distance between two adjacent flanges.

The circumferential length of the or each flange may be substantially the same as the distance between two guiding formations thereby causing the or each flange to move along the guiding formations when the container and closure are closed together.

The container may have a volume sufficient to contain the condensate generated during a typical duration of use of the respiratory system. The container may have a volume that is sufficiently low not to significantly or adversely affect the pressure or flow waveform of inspiratory gas delivered to a patient.

According to another aspect, there is provided a breathing limb, such as an expiratory limb, of a respiratory therapy system and the fluid trap of any of the above statements.

According to a further aspect, the invention may broadly be said to consist of a fluid trap for a breathing limb of a respiratory therapy system, comprising:
 a container configured to contain fluid received from the breathing limb;
 a closure, the closure and container being configured to be removeably mounted together to close the container; and
 a flexible member configured to be removeably mounted between the container and the closure; wherein
 the container, closure and flexible member are separate components each of which can be separated from the others.

According to another aspect there is provided a respiratory therapy system comprising the fluid trap of any one of the above statements.

The respiratory therapy system may comprise the fluid trap of any one of the above statements and any one or more of:
 a. a gas humidifier;
 b. a breathing limb comprising an inspiratory gas delivery conduit, which may or may not be heated;
 c. a breathing limb comprising an expiratory gas conduit;
 d. a breathing limb comprising a catheter mount; and/or
 e. a patient interface.

The respiratory therapy system may comprise the fluid trap of any one of the above statements and any one or more of:
 a. a gas flow generator;
 b. a respiratory ventilator;
 c. a gases blender;
 d. a pressure relief valve; and/or
 e. an expiratory pressure device that receives expiratory gases from an expiratory circuit and regulates expiratory gases to a positive end expiration pressure.

The expiratory pressure device may be further configured to generate pressure oscillations in use as a patient breathes. The expiratory pressure device may further comprise a container and a volume of water.

According to another aspect of the invention there is provided a circuit kit for use with a respiratory therapy system comprising the fluid trap as per any one of the above statements and any one or more of:
 a. a breathing limb comprising an inspiratory circuit;
 b. a breathing limb comprising an expiratory circuit that may, in some examples, be formed from, or include, one or more breathable regions through which water vapour can pass;
 c. a breathing limb comprising a catheter mount;
 d. one or more connectors or adapters;
 e. a humidifier chamber;
 f. a wye piece;
 g. a pressure line;
 h. a patient interface; and/or
 i. a pressure relief valve.

Further aspects of the invention, which should be considered in all its novel aspects, will become apparent from the following description. The term respiratory therapy system also encompasses a respiratory humidification system that is configured to provide heated, humidified gases to a patient or user. A respiratory humidification system may simply provide heated, humidified gases to a patient for respiratory comfort. A respiratory therapy system is any system that provides respiratory therapy of some sort with or without humidification of gases. Respiratory therapy system as described herein includes respiratory humidification systems.

DESCRIPTION OF THE DRAWINGS

A number of embodiments of the invention will now be described by way of example with reference to the drawings in which.

DETAILED DESCRIPTION OF SPECIFIC EMBODIMENTS

Figure 1:
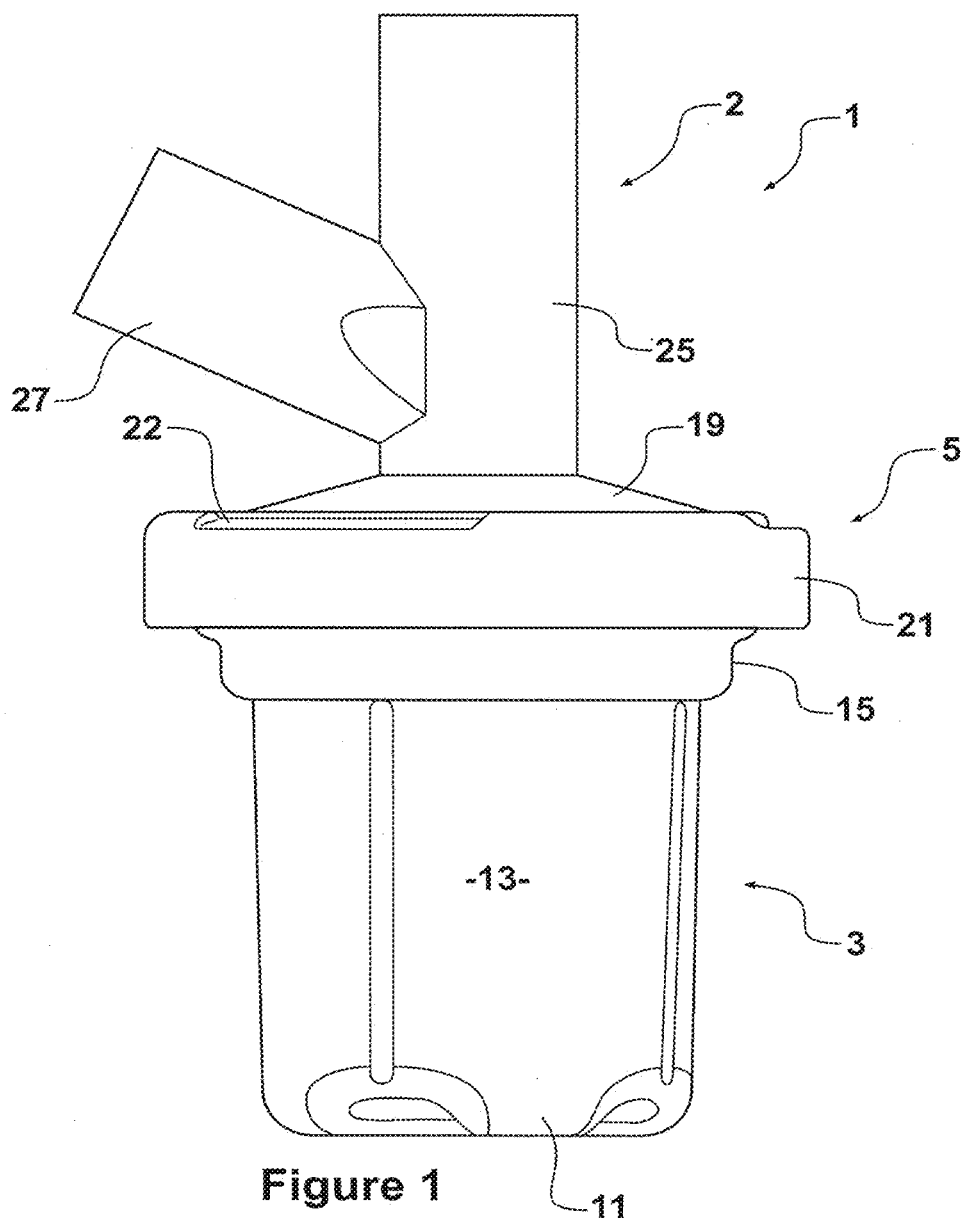
FIG. 1 is a side view of a fluid trap in accordance with the present disclosure.

With reference to the Figures a fluid trap 1 for a breathing limb, such as an expiratory limb, of a respiratory therapy system (not shown) comprises:

at least one inlet 2 configured to be connected to the breathing limb to receive fluid from the breathing limb;

a container 3 configured to contain fluid received from the inlet 2;

a closure 5, the closure 5 and container 3 being configured to be removeably mounted together to close the container 3; and a valve 7 configured to be removeably mounted on at least one of the container 3 and the closure 5, and configured to be in a closed condition which prevents fluid from being received in the container 3 from the inlet 2 when the closure 5 is not mounted on the container 3, the valve 7 being further configured to be in an open position which allows fluid from the inlet 2 into the container 3 when the closure 5 is mounted on the container 3. "Fluid trap 1" may also be referred to herein as a "water trap 1", "fluid trap 1", "reusable fluid trap 1", and/or "trap 1".

The container 3 in this example is substantially cylindrical and comprises a base 11 and an upstanding side wall 13. "Base 11" may also be referred to herein as a "container base 11". The upper margin of the side wall 13 terminates in an outwardly flared mouth portion 15. "Mouth portion 15" may also be referred to herein as "container mouth 15" and/or "mouth 15". A plurality of radially outwardly extending flanges 17 extend from a peripheral lip 18 of the mouth portion 15. Individual flanges of the "flanges 17" may also be referred to herein as "flange 17" or "flange section 17".

The closure 5 in this example is also substantially circular in plan and comprises a frustro-conical top 19 and a peripheral downwardly directed skirt 21 extending from the top 19. Alternatively, top 19 may be substantially planar in profile, or any other shape of profile such as domed, pyramidal, or triangular in profile. A plurality of arcuate slits 22 are formed in the top 19 adjacent the perimeter of the closure 5. The closure 5 further comprises the inlet 2. The inlet 2 comprises a first tube 25 which extends through the top 19 coaxially with the longitudinal axis of the trap 1, and a second tube 27 which extends into, and is inclined relative to, the first tube 25. Gases from the patient are received from the second tube 27 and exit from the first tube 25.

Whilst the overall shape of container 3 is substantially cylindrical in this described embodiment, and closure 5 is circular in plan, this and any of the other described embodiments of a container and closure can include other shapes of each feature, such as substantially polyhedral or substantially prismatic containers with closures having a plan of corresponding shape geometry. For example, the container could be cuboidal with a lid that is oblong or square when viewed in plan. Further, whilst the relationship between the inlet 2 and top 19 is preferably coaxial, alternative embodiments include non-co-axial relationships, such as an embodiment wherein an inlet is offset from the longitudinal axis of the lid and/or wherein an inlet is non-parallel with the longitudinal axis of the lid.

The first tube 25 and second tubes 27 are configured to be connected to, or at least be in fluid communication with, the expiratory limb of the breathing circuit such that condensate and other fluid in the expiratory limb can flow into the trap 1 via inlet 2. The trap 1 may therefore be connected directly to tubes of the expiratory limb, or directly to intermediate connectors or wye-pieces that are in fluid communication with the expiratory limb, or to a catheter mount that is in fluid communication with the expiratory limb. In an embodiment where the trap 1 is positioned along the expiratory path, a first expiratory conduit or gases circuit connects to the second tube 27 and the patient and second expiratory conduit or gases circuit connects to the first tube 25 and the ventilator. The expiratory circuit is therefore broken with the fluid trap 1 located part way along the length of the expiratory circuit. Therefore there is a first section of expiratory conduit from the patient which connects to the second tube 27. There is a second section of expiratory tube that extends from the fluid trap 1 and connects to the first tube 25, upwardly toward the ventilator.

Condensate and other fluids run from both expiratory tubes into the water trap 1. The water trap 1 is positioned such that the expiratory tubes are angled downward to the water trap such that fluids run downward into the water trap due to gravity. The lower end of the inlet 2 either defines, or is provided with, a valve seat 24 against which a valve seal of valve 7 seals. However, it is true that any fluid collected in the section of expiratory tube extending outwardly from the second tube 27 is also collected in the water trap because the expiratory limb connected to the second tube 27 extends upwardly so that any liquid in this second section of expiratory tube will run downward toward the water trap 1 due to gravity.

In one embodiment, water trap 1 is located below the ventilator (remote from the patient), so that the section of the expiratory tubes extending outwardly from the second tube 27 comes in from the patient at a downward angle, and the section of the expiratory tubes extending outwardly from the first tube 25 to the ventilator goes straight up/vertical to the ventilator for better draining angles and a more aesthetically appealing bedspace appearance.

The valve 7 is formed as a unitary member from a resiliently deformable material and is configured to be positioned between, and to engage with, both the container 3 and the closure 5. The valve 7 in this example is a mushroom valve comprising a valve base 29, an upstanding valve outer wall 31 and a lip 33 extending radially outwardly from the upper margin of the valve outer wall 31. The valve base 29 is substantially frustro-conical with a raised centre portion from which a central projection in the form valve stem 35 projects. The end of the valve stem 35 terminates in a valve disc 37, which is substantially cylindrical, and is configured to seal with the inlet 2. The underside of the raised centre portion comprises a downwardly directed hollow boss 39. As can best be seen from FIGS. 8 and 9 the valve 7 in this example is thus substantially 'W' shaped in transverse cross section.

The container 3, closure 5 and valve 7 are configured such that when the closure 5 is fully mounted on the container 3, the valve 7 is open such that it does not seal with the valve seat 24, such that fluid from the expiratory limb portions can flow through the first tube 25 and second tube 27, through the closure 5 and into the container 3.

The container 3, closure 5 and valve 7 are further configured such that when the closure 5 is not fully mounted on the container 3, the valve 7 is closed such that it does seal with the valve seat 24 such that fluid from the expiratory limb cannot flow into the container 3. Thus, when the container is not present the expiratory limb remains sealed such that gas flowing through the expiratory limb does not leak through the valve seat 24.

The container 3, closure 5 and valve 7 are so configured as above because the resiliently deformable material of the valve 7 deforms and changes shape as the closure 5 and container 3 are moved together towards a fully mounted condition. The 'W' shaped profile of the valve 7 also facilitates the spring like behaviour. The container 3 engages a lower pan of the valve 7 and the closure 5 engages an upper part of the valve 7. This engagement forces the upper and lower parts of the valve 7 towards one another, which deforms the valve base 29, forcing the raised centre portion and the valve stem 35 towards the inlet 2 such that the valve disc 37 is received in the lower end of the first tube 25, with the valve disc 37 above the valve seat 24, as can be seen from FIG. 10. The valve disc 37 rests on top of the valve seat 24 and sealingly engages with the valve seat 24 to seal the inlet 2, when the container 3 and closure 5 are not sealingly mounted together. The valve disc 37 is pushed through the valve seat 24 each time the closure 5 and container 3 are mounted together. This can be achieved via an upwardly directed force applied to the boss 39 for example. Following that the valve disc 37 never drops below the valve seat 24 unless disassembled.

The internal walls of the mouth portion 15 of the container configured to receive valve 7 are outwardly flared such that the valve base 29 is squeezed inwardly as the valve 7 and container mouth portion 15 are progressively engaged. The 'W' shaped profile of the valve 7 is such that that lateral squeezing of the valve base 29 forces the raised centre portion and valve stem 35 upward toward the inlet 2 such that the valve disc 37 may be received in the lower end of the first tube 25, with the valve disc 37 above the valve seat 24, as can be seen from FIG. 10.

Three Part Fit

The fluid trap 1 comprises three fully separable primary components, specifically including valve 7, which is fully removable. The three-piece design, including a closure 5 with collection ports or first tube 25 and second tube 27, a valve 7, which is flexible, and a container 3 comprising a collection cup, allows relatively easy reprocessing, and limits the areas in which potential harmful pathogens can accumulate and grow. The three part arrangement, and in particular the totally separable valve, container and closure, mean that all the parts that come into contact with fluids can be reprocessed, including being able to be sterilized with a suitable process such as autoclaving. Moreover the three part design of this embodiment is useful for easy assembly and disassembly for nurses or other carers when emptying the trap 1, which provides a benefit for both reusable and disposable embodiments of this disclosure.

The three primary components have generally planar surfaces, with sharp radiuses or crevices being minimised, thus reducing the possibility for, and locations of, pathogen accumulation and pathogen growth.

To minimize corners and crevices, the components include radiused corners for smooth transitions between adjacent surfaces. Although many shapes of containers and closures may be used, a generally cylindrical shape can help to avoid such corners and crevices.

This arrangement includes a middle member being valve 7 made of a flexible or resilient material, which as well as performing the inlet valve function described above, serves to form a fluid seal between the container 3 and closure 5.

The valve 7 is formed from any suitable resiliently deformable material or combination of materials. Such a material may include any one or more of a plastic, rubber and silicone material or combination of materials. The valve 7 is formed from a material that can be used in a reprocessing procedure, and in particular can be suitably sterilized by a process such as by radiating, auto-claving, or gas sterilization for example. The material can be selected so that it does not breakdown or change shape or undergo any other significant deterioration, as part of reprocessing, which may include relatively high temperatures, relatively high pressures, and/or relatively harsh cleaning chemicals.

When the container 3 and the closure 5 are not mounted together, the valve 7 can be retained inside the closure 5, sealing against the skirt 21 of the closure 5 and also sealing against the valve seat 24 preventing the escape of exhaled air and depressurisation of the breathing circuit. The insertion of the container 3 into the closure 5 deforms the valve 7 in a predetermined way as described above, opening the valve 7 and forming a fluid connection between the expiratory circuit and the container 3. In particular, as the container 3 is inserted into the closure 5, the container 3 and closure 5 deform the valve 7 such that the valve stem 35 moves along the lower part of the first tube 25 of the inlet 2, moving the valve disc 37 away from the valve seat 24. As the container 3 is removed from the closure 5 (or vice versa), the valve 7 provides a spring force that pulls the valve 7 downwardly, when viewing the fluid trap 1 in the orientation shown in the figures. There is a spring force or biasing force caused by the shape, configuration and material of the valve body that pulls the valve disc 37 downward and causes sealing against the valve seat 24 when the closure 5 and container 3 are unbound or disconnected from each other. The rest position of the valve 7 is against the valve seat 24. The force of the container 3 being urged upward to engage the closure 5 is greater than the biasing force, hence the valve disc 37 is pushed upward as the container 3 and closure 5 are assembled together.

The container 3 may have a volume designed so that at a standard filling rate the container 3 only needs emptying once a shift, without having a compressible volume so large that it adversely affects the ventilator. The volume of the container 3 is large enough to reduce the amount of time the container 3 needs to be emptied during a therapy session, but also the volume is small enough such that the compressible volume of the container 3 is small enough such that the ventilator is not adversely affected and the pressure drop across the expiratory circuit is small enough such that ventilator function is not compromised. In one example the volume of the container 3 does not need to be emptied for at least an hour. In another form the container volume does not need to be emptied for 15 mins to 30 mins. A smaller container volume can be used for neonatal humidification or neonatal respiratory therapy. A larger container volume can be used in adult humidification or adult respiratory therapy.

In the example where the fluid trap is used in a catheter mount, the container 3 may have a volume that is small enough to ensure that the inspiratory gas flow or pressure waveform is not significantly or adversely affected. A fluid trap used in a catheter mount may be configured such that the container 3 comprises a volume that may only be required to be emptied once or twice during therapy.

In some examples, the container 3 has a volume that is large enough that the container 3 does not need to be emptied for one therapy session, while still being small enough such that the compressible volume does not adversely affect the ventilator.

The container volume could be large enough that the container 3 can be used for up to an hour without emptying, or up to 2 hours without emptying, or within 1 to 10 hours without emptying.

Different therapies may employ different volume containers. For example, in neonatal humidification or invasive ventilation for neonates, the container volume would be smaller than that for adult invasive ventilation. For neonate invasive therapy the container may only be used for 15 mins to 30 mins before emptying. For neonate therapies the volume of a container is desirably smaller to ensure there is not a significant pressure drop due to the volume of the container.

Container-Closure Connection

The closure 5 could be removeably mounted on the container 3 using any of a taper, snap, push or screw fit as the connection mechanism between the two components. The current disclosure encompasses connection mechanisms of these types. However, these types of connection mechanism can include disadvantages such as requiring significant force in the direction of removal (taper, snap and push type mechanisms), not being feasible with the container/closure materials used (snap type mechanism), or significantly increasing the tooling cost required to create the connection mechanism (screw type mechanism). Further some of these closure types require relatively complex tooling techniques/relatively complex manufacturing techniques. Some of these connection types may provide spaces for pathogen accumulation and growth due to the connection types including areas that are difficult to clean or include sharp corners or crevices, such as, for example, screw threads. The connection mechanism is preferably configured such that the connection provides a fluid tight connection such that no fluid, and in particular no liquid, leaks from the container 3 via the closure 5 or the interface between closure 5 and container 3.

In the above example, the fluid trap 1 uses a push-rotate fit connection mechanism. This may help to reduce the risk of spillage during the removal of the container 3 after use, as the forces generated during assembly and disassembly of the trap 1 are rotational, and do not result in potential for rapid movement once the container 3 comes loose from the closure 5 (or vice versa).

Additionally, the engaging parts of the three primary components of the container 3, closure 5 and valve 7 are such that assembly or reassembly of the fluid trap 1 is not possible in an incomplete state—that is, the container 3, closure 5 and valve 7 must all be present or (re)assembly is not possible. In a preferred embodiment, this is enabled by the valve 7 forming an intermediate component located between, and engaging both of, the container 3 and the closure 5. This engagement between the container 3, closure 5 and valve 7 may be a frictional engagement between smooth/planar surfaces of the components so as to provide the friction required to hold the push-rotate connection in place. However, alternative solutions may be employed without departing from the nature of the disclosure. For example, the valve 7 and/or container 3 and/or closure 5 could be provided with engagement formations such as threaded or snap fit formations or clips or tabs.

Further, the container 3 and/or the closure 5 may be provide with guiding/locating features configured to guide the closure 5 and the container 3 together.

One of the container 3 and closure 5 comprise one or more guide formations configured to engage with, and guide, projections, such as flanges, on the other of the container 3 and closure 5, as the container 3 and closure 5 are mounted together.

Figure 2:
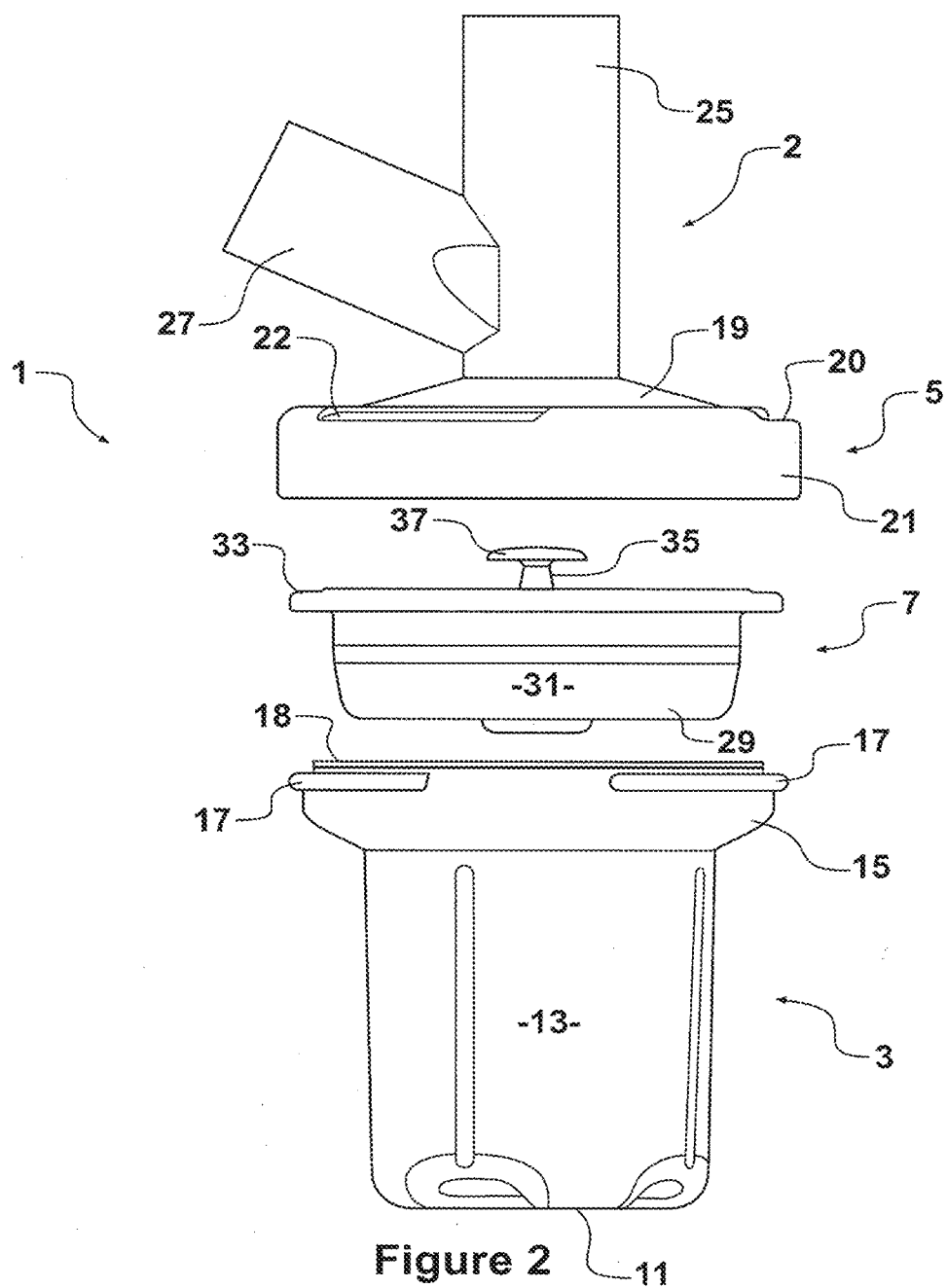
FIG. 2 is an exploded side view of the trap of FIG. 1.
Figure 3A:
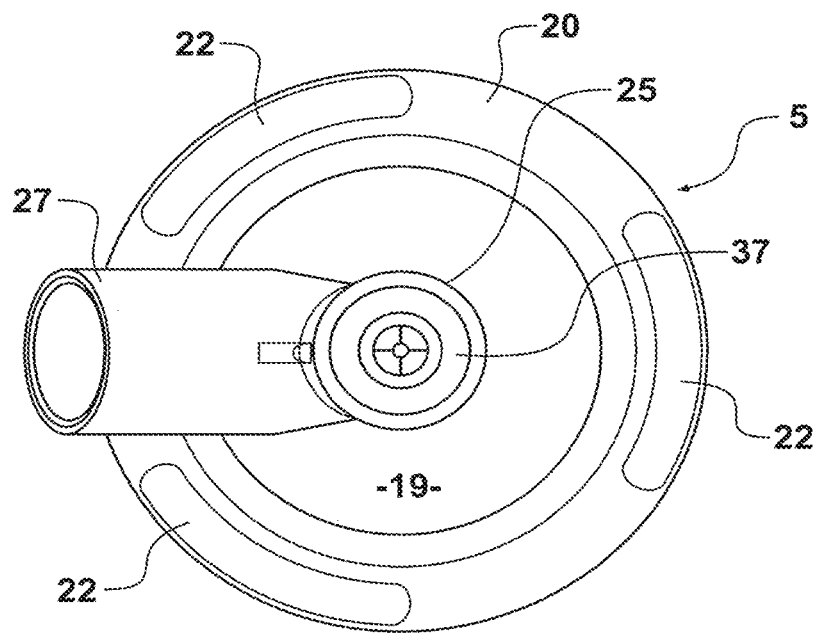
FIGS. 3a and 3b are plan views of the trap of FIGS. 1 and 2, being line and shaded versions respectively.
Figure 3B:
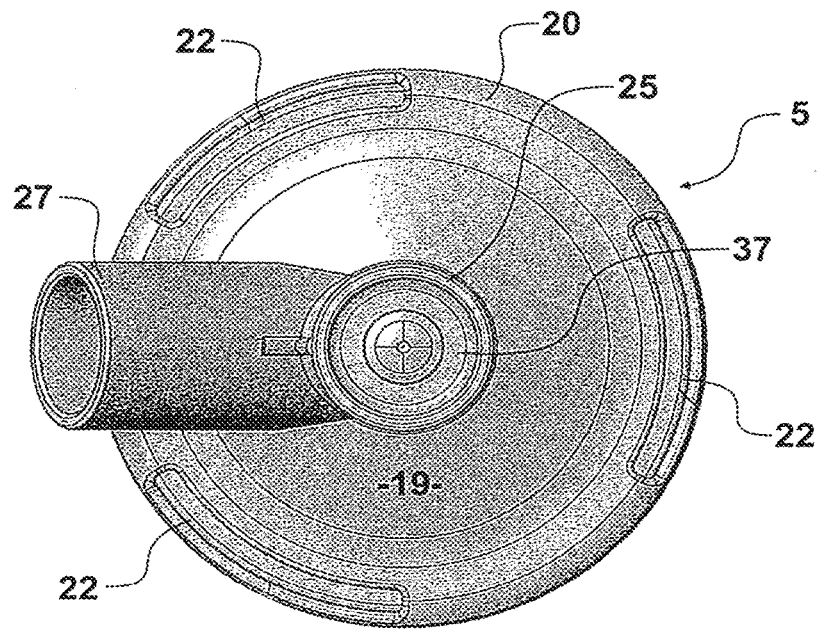
Figure 11:
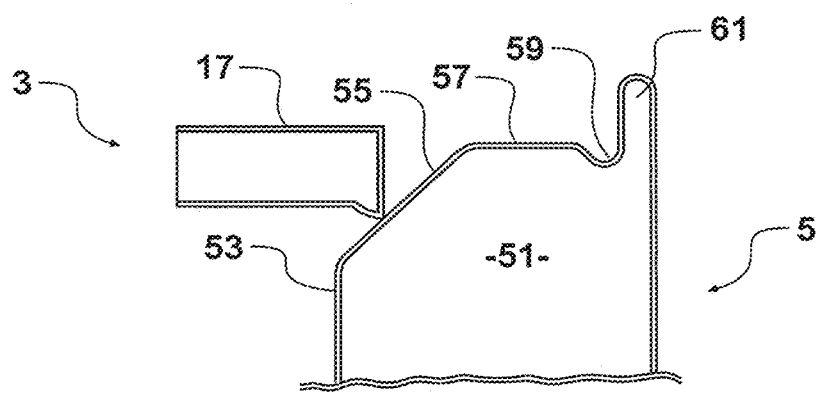
FIG. 11 is an enlarged sectional schematic side view of a of the container, closure and valve of the trap of FIGS. 1 to 10.
Figure 12A:
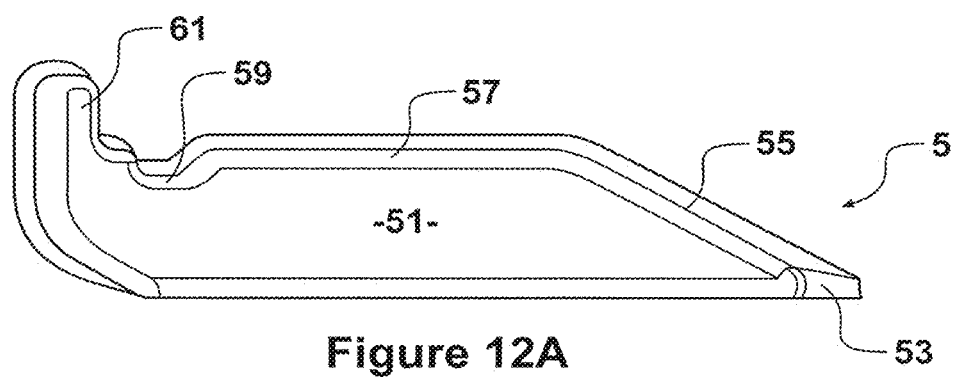
FIGS. 12a and 12b are enlarged sectional side views of part of the container, closure and valve of the trap of FIGS. 1 to 11, being line and shaded versions respectively.
Figure 12B:
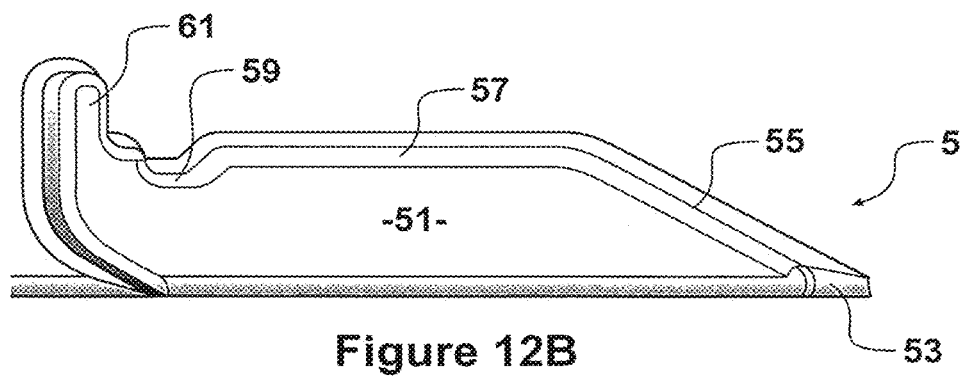

In one example, and with particular reference to FIG. 11, the closure 5 includes the requisite features for a push-rotate fit which are designed to interface with projections being flanges 17 projecting from the container 3 and shown in FIG. 2. In this example the container 3 comprises the projections which are configured to engage with, and be guided by, guide formations provided on the closure 5. The or each guide formation comprises a guide surface that assists the flange section 17 to move upward onto the ramp section.

In this example, the downwardly directed skirt 21 of the closure 5 is provided with a plurality of guide formations 51 which extend radially inwardly of the skirt 21. Each guide formation 51 comprises an outer guide surface 53, which may be substantially vertical, the outer guide surface 53 leading to a radially inwardly and upwardly inclined ramp portion 55 and a radially inwardly extending horizontal land portion 57. The radially inward end of the land portion 57 terminates in a security formation comprising a depression 59 which may be in the form, for example, of a peripherally extending channel or one or more discrete dimples. A vertically upwardly extending end stop 61 is provided adjacent the depression 59.

Prior to assembly the mouth 15 of the container 3 is located concentrically within the skirt 21 of the closure 5, with the lower edge of the closure skirt 21 adjacent the flanges 17. Each flange 17 is located between adjacent guide formations 51 on the closure skirt 21. The outer guide surface 53 is preferably a surface that assists the flange section 17 to move upward onto the ramp portion 55.

As the container 3 is pushed axially into the closure 5, the container 3 is simultaneously rotated relative to the closure 5. This rotates the flanges 17 of the container 3 up the guide formations 51 of the skirt 21 of the closure 5, and in particular up outer guide surface 53 and onto ramp portion 55. This further guides the flanges 17 of the container 3 onto land portion 57 and ultimately a radially outermost part of the flanges 17, which may comprise a peripheral ridge or protuberance, is received in depression 59 with the radially innermost part of each guide formation 51 abutting the end stop 61. End stop 61 prevents further relative axial movement between the container 3 and the closure 5. This is important to ensure that the valve 7, which is sandwiched between the container 3 and closure 5, is in the correct position and is not overly compressed or deformed. The engagement between the skirt 21 and the depression 59 provides an audible and/or tactile indication that the container 3 and closure 5 are correctly located and that the container 3 is sealed with the closure 5. The length of the skirt 21 is longer or equal to the distance between a pair of guide formations. This ensures that when the container 3 is vertically urged against the closure 5, each flange 17 is pushed up the ramp portion 55 of the respective guide formation 51. The closure 5 may comprise two or more guide formations 51. Preferably the closure 5 comprises three guide formations 51 that are equispaced around the circumference of the closure 5. In this example, the container 3 comprises three flanges 17, also equispaced about the circumference of the container 3.

The or each guide formation 51 further serves to guide the container 3 into the closure 5 in a linear/concentric fashion; preventing or at least minimising unwanted deformation of the valve 7. Ramp portion 55 guides the container 3 upwards as it is rotated; allowing an easier assembly and tighter seal between all three primary components. The length of the closure skirt 21 being greater than or equal to the distance between each guide formation 51 also helps the flanges 17 to engage the guide formations 51 when the closure 5 is brought into contact with the container 3. This ensures linear movement of closure 5 and linear movement of the valve 7.

The closure 5 is designed such that the valve 7 sits between the closure 5 and the end stop 61 of the container 3, allowing the valve 7 to rest on these features. This feature additionally causes the push-rotate action to fail when the valve 7 isn't present, as the container 3 and closure 5 will not form a stable connection without the valve 7.

In an alternative embodiment, the or each guide formation 51 is formed on the mouth of the container 3. In this alternative embodiment the flanges 17 may be formed on the closure 5 and the guide formations can be formed on the mouth 15 or on or adjacent the peripheral lip 18 of the container 3, such that the flanges 17 contact and interact with the guide formations 51 to assist in engaging the closure 5 and the container 3, in the same way as described above.

Prior to assembly the mouth 15 of the container 3 is located concentrically within the skirt 21 of the closure 5, with the lower edge of the closure skirt 21 adjacent the outer guide surface 53. Each flange 17 on the closure skirt 21 is located between adjacent guide formations 51 on the container 3.

Subsequent assembly is as described in the embodiment above where the flanges 17 are provided on the container 3. The guide formations 51 serve to engage and guide the flanges 17 as the container 3 and closure 5 are pushed and rotated together.

Sealing

The seal of the fluid trap 1 between the container 3 and closure 5 is enabled by a combination of sealing formations which in this example comprise raised half a-rings 63, 65 on the container 3 and on the valve 7. The a-ring 63 is formed on the peripheral lip 18 of the mouth 15 of the container 3. The a-ring 63 may be a separate component, or may be integrally formed on the peripheral lip 18. The a-ring 63 may be of a resiliently deformable and/or relatively soft material that is overmoulded or adhered to the peripheral lip 18. Alternatively the o-ring 63 may be of a rigid material that is moulded to the peripheral lip 18.

Sealing between the closure 5 and valve 7 is further provided by a flattened section 20 of the closure 5 directly above and concentric with the half a-rings 63. The half a-ring 65 of the valve 7 flattens and seals against flattened section 20 of the closure 5. The half a-ring 65 is made from a resilient material and may be made of the same resilient material as the valve 7. Preferably the half a-ring 65 is integrally formed in the valve. The raised a-ring 63 on the container 3 provides increased pressure in the region of the a-ring 63. The raised a-ring 63 on the container is a rigid and bears against the valve to deform the valve and create a seal. In the preferred embodiment, the force to create the seal is provided when the container 3 is pushed up into the closure 5 during the initial stages of assembly. Additional force that helps provide a tighter seal may be provided by rotation as the container 3 is pushed up with the closure skirt 21 engaging the ramp portion 55 of the outer guide surface 53.

In this example, the closure skirt 21 is outermost with the mouth 15 of the container 3 being received concentrically within the closure skirt 21. Alternatively, the mouth 15 of the container 3 could be radially outermost with the closure skirt 21 being inside the container mouth 15.

The valve 7 is configured so as to provide a seal between the valve disc 37 and the valve seat 24 to seal off the gases pathways comprising first tube 25 and second tube 27 and prevent potentially hazardous liquids/condensate leaking onto the floor, for example. As can best be seen in FIG. 10, the valve disc 37 is pulled downward onto the valve seat 24 when the container 3 is disengaged from the closure 5, thus sealing the inlet 2 to prevent liquids and/or condensate from leaking from the expiratory limb, and spilling through the inlet 2. This automatic, or default, sealing closed of the inlet 2 serves to improve the ease of use and hygiene of the fluid trap 1.

Seal Motion

Figure 9A:
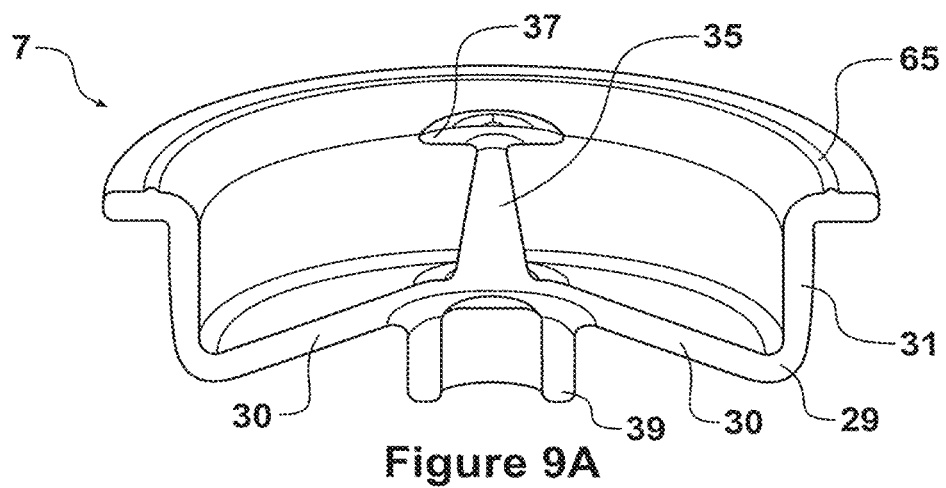
FIGS. 9a and 9b are sectional perspective views from the top of the valve of the trap of FIGS. 1 to 8, being line and shaded versions respectively.
Figure 9B:
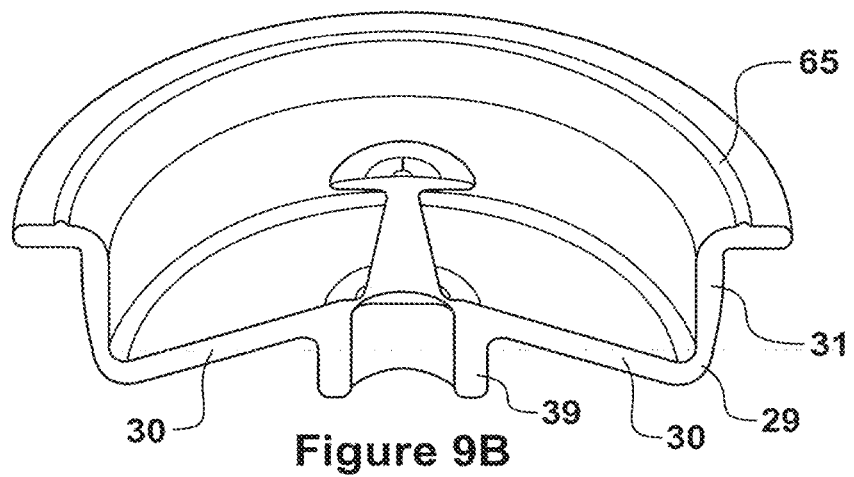

The sealing forces may be generated via the motion of various parts of the valve 7 that are moved by the container 3 and/or the closure 5 as the two components are mounted together. In a preferred embodiment as described above, the valve base 29 moves such that the raised centre portion from which the valve stem 35 projects moves upwardly. Referring in particular to FIG. 9, when viewed in transverse cross section the frustro-conical portion of the valve base 29 comprises upwardly inclined portions or arms 30. The angle of inclination of these inclined portions 30 is such that these inclined portions 30 function as a cantilever hinged about the outermost and lowermost portions of the valve base 29. Thus as these lowermost portions of the valve base 29 engage with the mouth 15 of the container 3, this squeezes those lowermost portions of the valve base 29 between the container mouth 15 and the underside of the closure 5, pivoting the inclined portions 30 upwardly such that the valve disc 37 moves upwardly out of sealing engagement with the valve seat 24. As the lowermost portions of the valve base 29 engage with the mouth 15 of the container 3, this squeezes the lowermost portions of the valve base 29 inwardly between the flared walls of the mouth 15 such that the inclined portions 30 are pivoted upwardly. The geometry of the valve 7 contributes to the attributes of the above described movement and spring back force of the valve 7. Pressure on the bottom of the W shape squeezes the central member upwards with a motion defined by the length of travel between closure initial contact with the valve 7 and when the closure 5 is fully mounted on the container 3.

In some embodiments, this pressure may be provided by contact with a section of the container 3 that is horizontal, with the ramp portion 55 of the closure 5, or in the preferred embodiment where there is a surface in the container 3 that slopes downwards at an angle for a predetermined length. In the preferred embodiment, contact with this surface pushes the lowermost section of the inclined portions 30 of the W of the valve 7 together, while simultaneously forcing those inclined portions 30 upwards. Alternative embodiments may achieve either of these motions.

This length of travel is confined such that no contact occurs between the main body of the valve 7 and the valve seat 24, yet the valve disc 37 is raised a significant distance, which may be approximately 10 mm in some examples, above the valve seat 24 in order to prevent condensation clogging the valve 7. The dimensions of the valve and the shape of the valve and its components are made such that the main body of the valve does not contact the valve seat. The valve 7 is made of a resilient material, and the valve is biased to move downward away from the valve seat such that the valve disc 37 moves downward and sits against the valve seat when the closure and container are disconnected. This ensures the fluid passage through the valve seat 24 is sealed by the valve disc 37.

While this embodiment has been described in terms of a W shaped valve 7, other shapes are possible. For example the valve may have a concertina section within it to promote resilient movement of the valve. Alternatively the valve may comprise a spring within it to allow resilient movement of the valve.

Central Actuator

In an alternative embodiment, the motion of the valve 7 is created by contact with a central actuator 85 provided on the container 3. The central actuator 85 may comprise an upstanding finger or lug which makes contact with the central part of the underside of the valve base 29, directly beneath the valve stem 35, and forces the valve stem 35 and valve disk 37 upwards as the container 3 is inserted into the closure 5. A central actuator 85 in this position may be used to prevent the valve 7 from deforming into unwanted configurations.

The central actuator 85 is configured to be resistant to any pressure that may be applied to it during reprocessing. Additionally, the central actuator 85 may be hollow and formed integrally from the surface of the container 3. Such a central actuator 85 is significantly stronger than a free standing central actuator, and provides an Obvious failure if the section broke. However, having an increased central actuator 85 volume negatively affects the volume in the container 3, requiring more frequent refills. The central actuator 85 is preferably thin and elongate in shape such that the central actuator 85 occupies as little volume within the container as possible. This ensures that the container still has a large enough volume to collect enough fluid during one therapy session without the need for changing or emptying and reduces any resistance to flow and pressure drop across the water trap, when in use.

In this embodiment, the valve 7 may have a profile in cross section that is similar to a V or—or U. Such a valve 7 will still need to spring back when the container 3 is removed, but does not need to make contact with the container 3 in any other location. In a further alternative form the valve 7 may have a flat base but still is formed to be biased to provide a spring back force on the valve disc 37.

Valve

The closure 5 includes several features that streamline reassembly, and the proper insertion of the valve disk 37 into the aperture formed by the valve seat 24.

Figure 8:
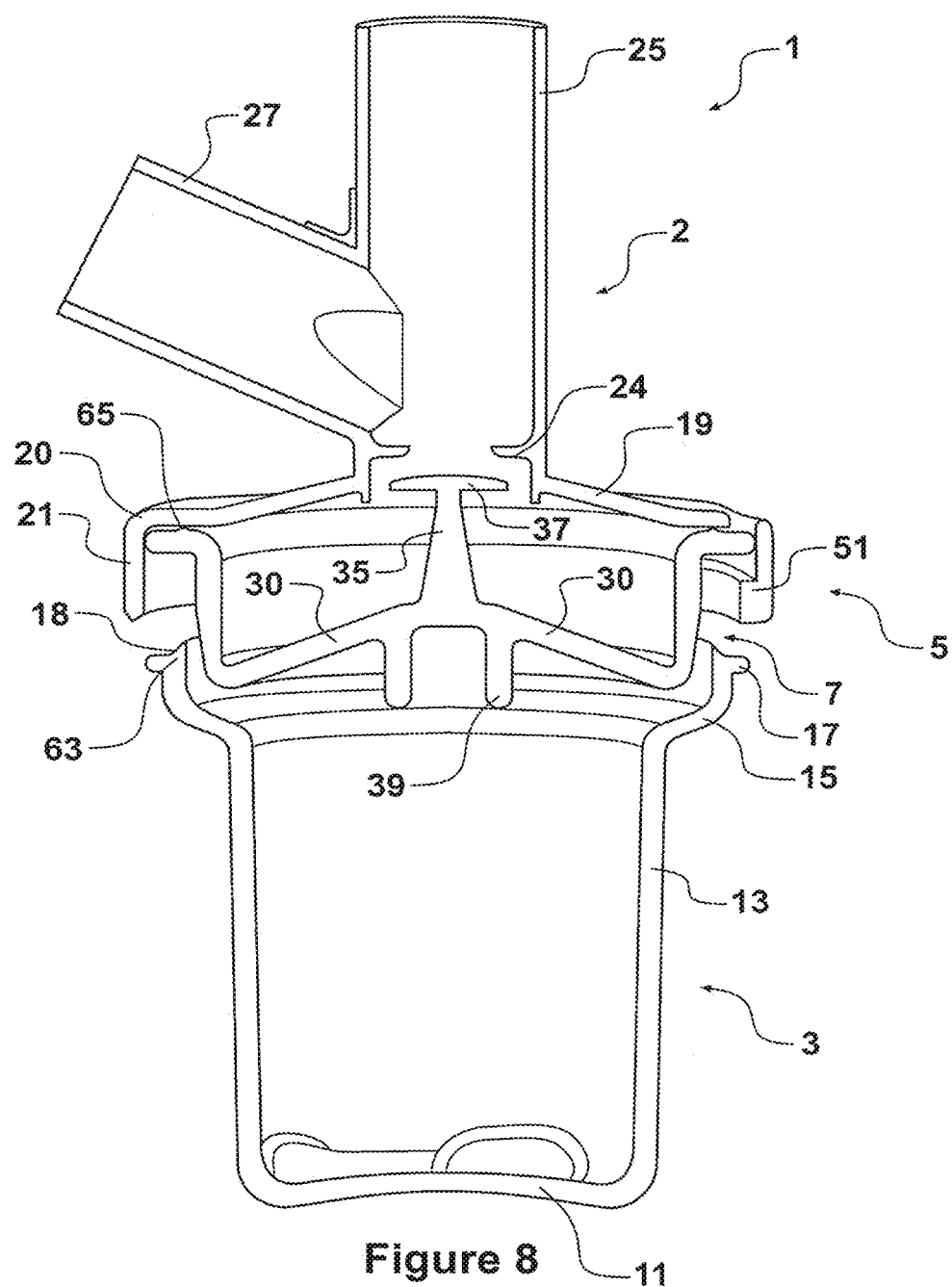
FIG. 8 is a sectional side view of the trap of FIGS. 1 to 7, with the closure, valve and container in a partially disassembled condition.
Figure 10:
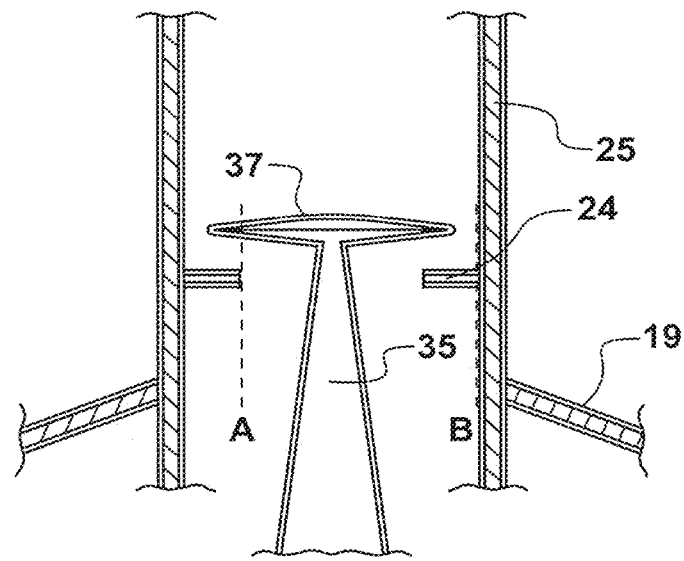
FIG. 10 is an enlarged sectional side view of part of the valve and closure of the trap of FIGS. 1 to 9.

With reference to FIGS. 8 and 10, the valve seat 24 may be formed at the lower end of the first tube 25 and comprise the under-surface of the closure 5. In the first example, to prevent kinking of the flexible valve stem 35, the angle between the valve stem 35 and the under-surface of the closure 5 is substantially 90 degrees, and the wall of the lower end of the first tube 25 is substantially parallel with the longitudinal axis of the valve stem 35. As a result, the lower end of the first tube 25 guides the valve disk 37 up to the valve seat 24.

The valve 7 further comprises a plurality of cut outs or recesses formed in the valve. The cut outs or recesses are preferably evenly spaced around the valve to ensure consistent and equivalent deformation of the valve when the closure 5 and the container 3 are engaged with each other. The cut outs or recesses may extend radially outwardly from the centrally positioned valve stem 35. The cut outs or recesses are formed in the inclined portions 30 of the valve 7. The cut outs and recesses may be triangular or trapezoidal or rectangular in shape. The cut outs or recesses improve the flexibility of the valve. The cut-outs or recesses are also configured to allow fluid flow or fluid transfer from the closure to the container. The cut-outs are large enough to provide no or low impedance to flow between an inlet and the container, while maintaining a biasing force of the valve such that the valve rests against a valve seat when the container and closure are disengaged. In an alternative form the cut outs or recesses may be in the form of circles. In this alternative form the cut outs or recesses are disposed on the inclined portions 30 and are arranged concentrically around the valve body with a centre at the valve stem 35. In this alternative form the cut outs or recesses are concentric circles that are arranged on the valve and improve flexibility of the valve, while providing areas for fluid to drain from the first tube 25 and second tube 27 into the container 3. In a further alternative form the cut outs or recesses may be unevenly spaced around the valve.

In another embodiment, and with reference to FIG. 8, the valve seat 24 may be provided inside the lower end of the first tube 25 (below where it is shown in the embodiment of FIG. 8) such that the valve seat 24 is spaced below the under-surface of the closure 5 to provide an alternative location for the valve disk 37 to sit.

The bottom of the valve seat 24 may include multiple ridges, for example three in a preferred embodiment, designed to manipulate the valve disc 37 in such a way that it folds easily with minimum deformation and/or minimum resistance/effort while passing through the valve seat 24 during assembly. The three ridges under the valve seat cause localized deformation of the valve disc 37 around the ridge, thereby reducing the force required to push the valve disc through the valve seat. Additionally, there is an important ratio between the size of the valve disc 37 and the hole in the valve seat 24, where the width of the valve disc 37 is greater than the distance A-B shown in FIG. 10. The distance A-B is the distance, when viewed in transverse cross section, between the inside edge of one side of the valve seat 24, and the opposed wall of the first tube 25. This size relationship prevents the valve disc 37 sitting unequally, or in a position where the pressure inside the system will force the valve disk 37 through the valve seat 24.

Additionally, there may be alterations so that the valve disk 37 passes onto the valve seat 24 immediately on insertion, rather than requiring the insertion of the container 3.

Other Features

The fluid trap could be reusable, in that the fluid trap could be suitable for multiple patient use and/or may be reprocessable. Alternatively, the fluid trap could be disposable, that is, single use.

The ease of use of the fluid trap 1 can be controlled by altering and optimising the features of the valve 7 and the features of the container 3 and closure 5 which interact with the valve 7. Desirably, these features are chosen to minimise the assembly force, while ensuring that the spring back force is sufficient to seal the valve 7 after removing the container 3. In particular it is desirable that when the container 3 is removed, the valve 7 deforms or moves the valve stem 35 such that the valve disc 37 seals against the valve seat 24 to seal the fluid passage through the valve seat 24 closed. Thus, when the container 3 is removed for cleaning/emptying, the closure 5 is sealed off from leaking condensate via the passage through the valve seat 24. Preferably the container 3, closure 5 and valve 7 comprise planar surfaces with smoothly radiused corners to make reprocessing easier and reducing the possible sites for pathogen accumulation and/or growth.

Figure 4A:
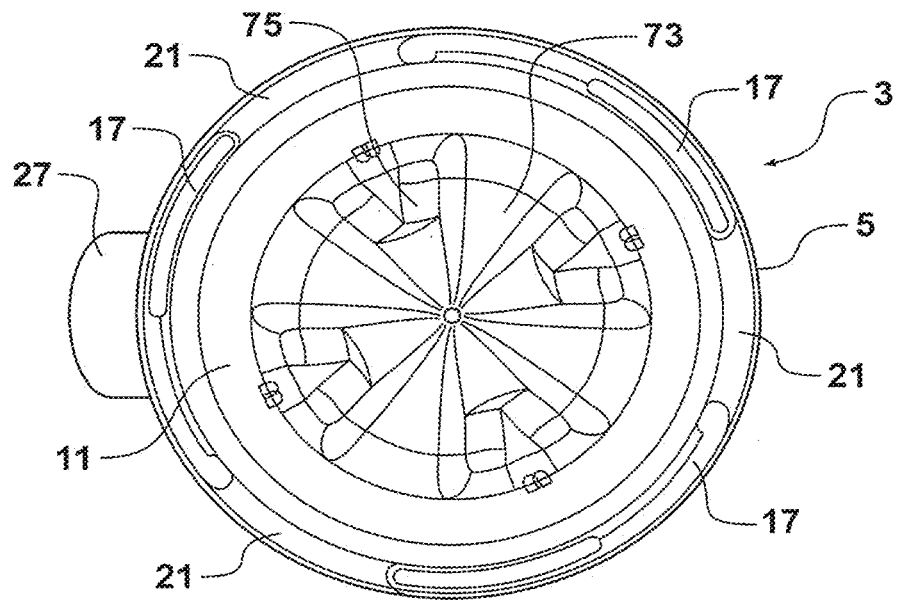
FIGS. 4a and 4b are bottom views of the trap of FIGS. 1 to 3, being line and shaded versions respectively.
Figure 4B:
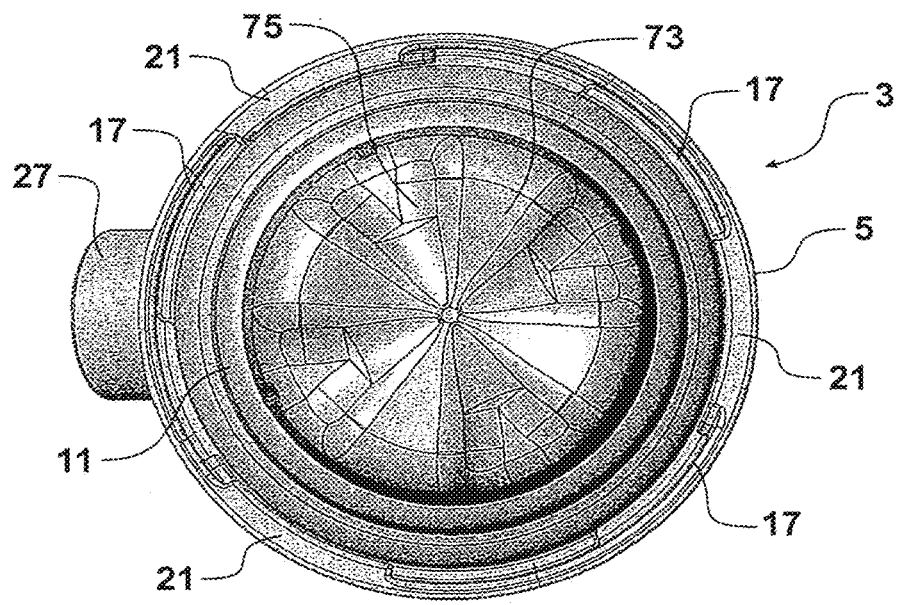
Figure 5A:
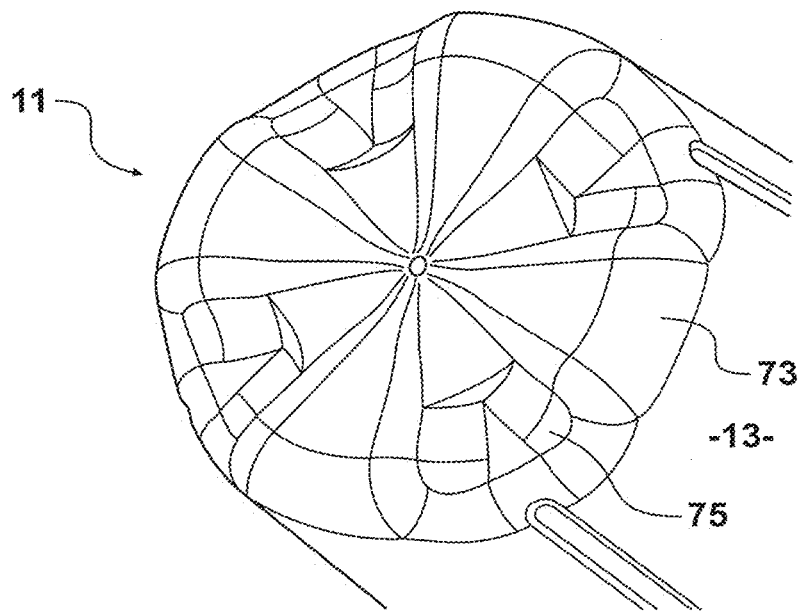
FIGS. 5a and 5b are perspective views from the bottom of the trap of FIGS. 1 to 4, being line and shaded versions respectively.
Figure 5B:
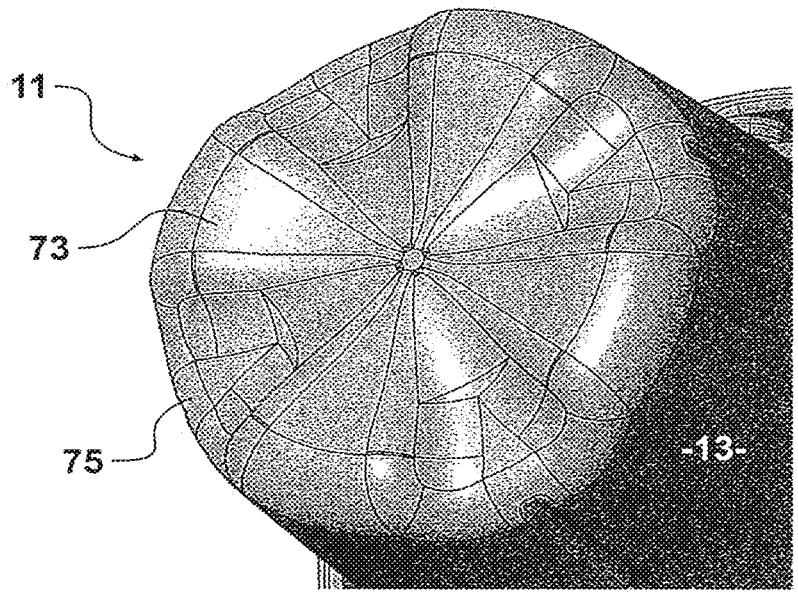
Figure 6:
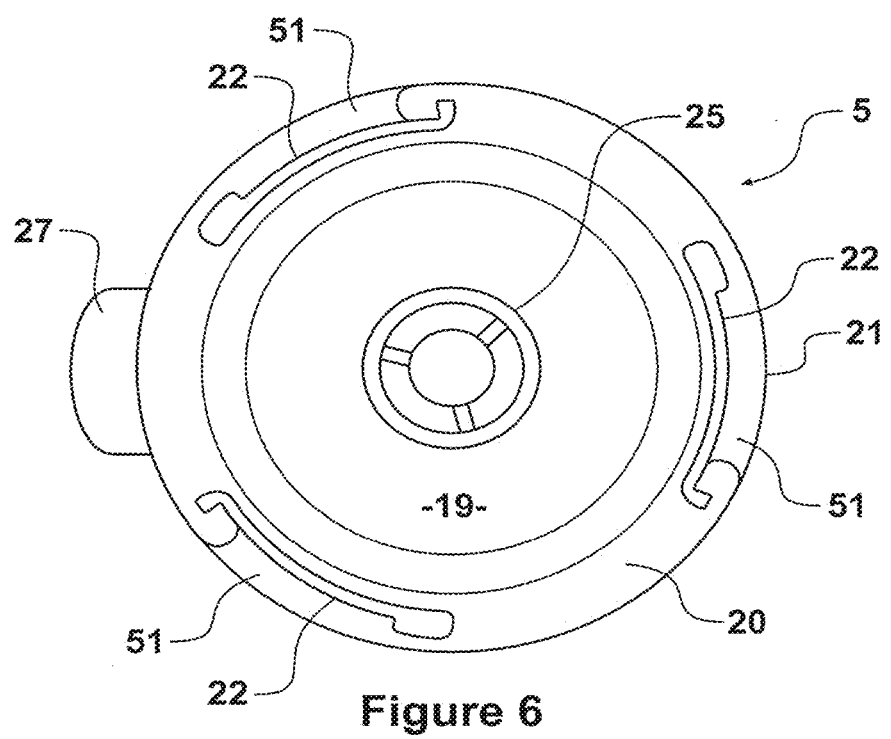
FIG. 6 is a view from underneath the closure of the trap of FIGS. 1 to 5.
Figure 7:
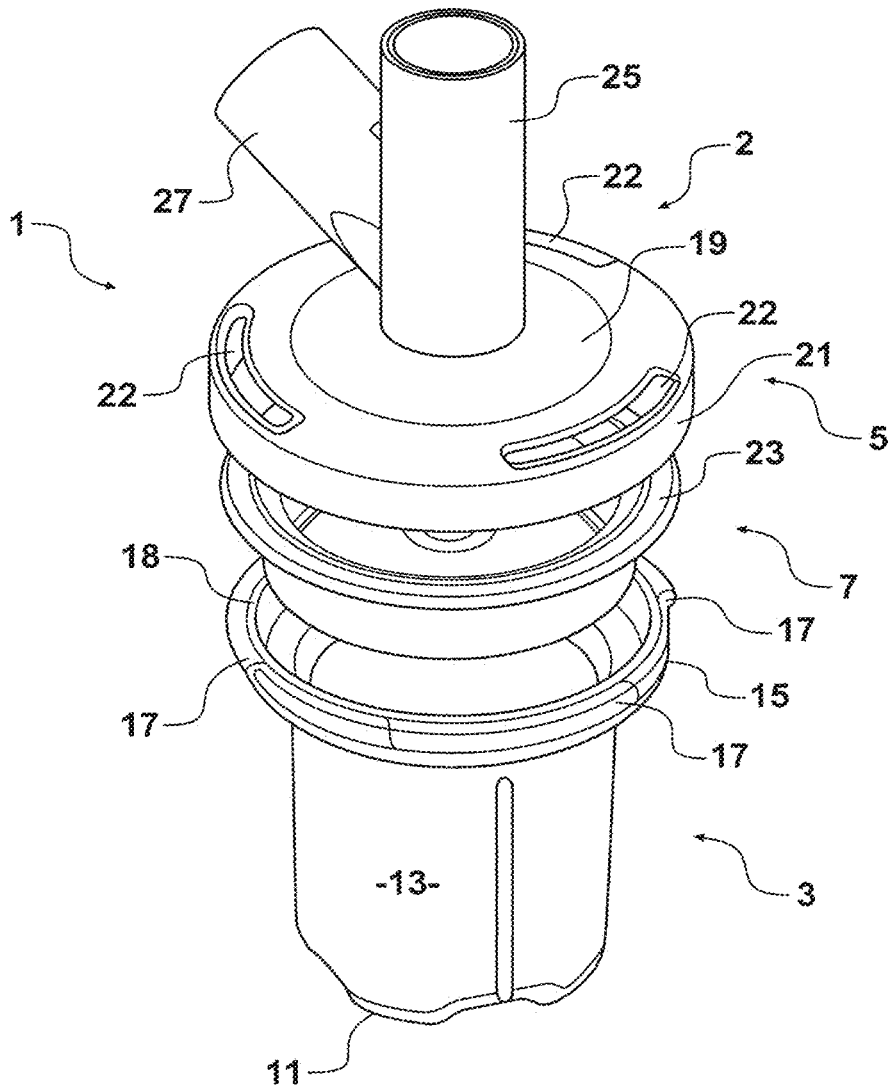
FIG. 7 is an exploded perspective view from the side and top of the trap of FIGS. 1 to 6.

Additionally, the shape of the container 3 may be such as to suggest the direction of twisting that is used to seal the fluid trap 1, and/or formed that there is no point where stagnant fluid may rest when the container 3 is placed in a certain orientation. In one example, and with reference to FIGS. 4 and 5, the base of container 3 is provided with a plurality of raised and recessed regions 73, 75, each region being a segment of the circular base when viewed from below. Such raised and recessed regions allow for draining fluid following reprocessing. These features can also promote the easy re-assembly of the components and reprocessing.

Figure 13:
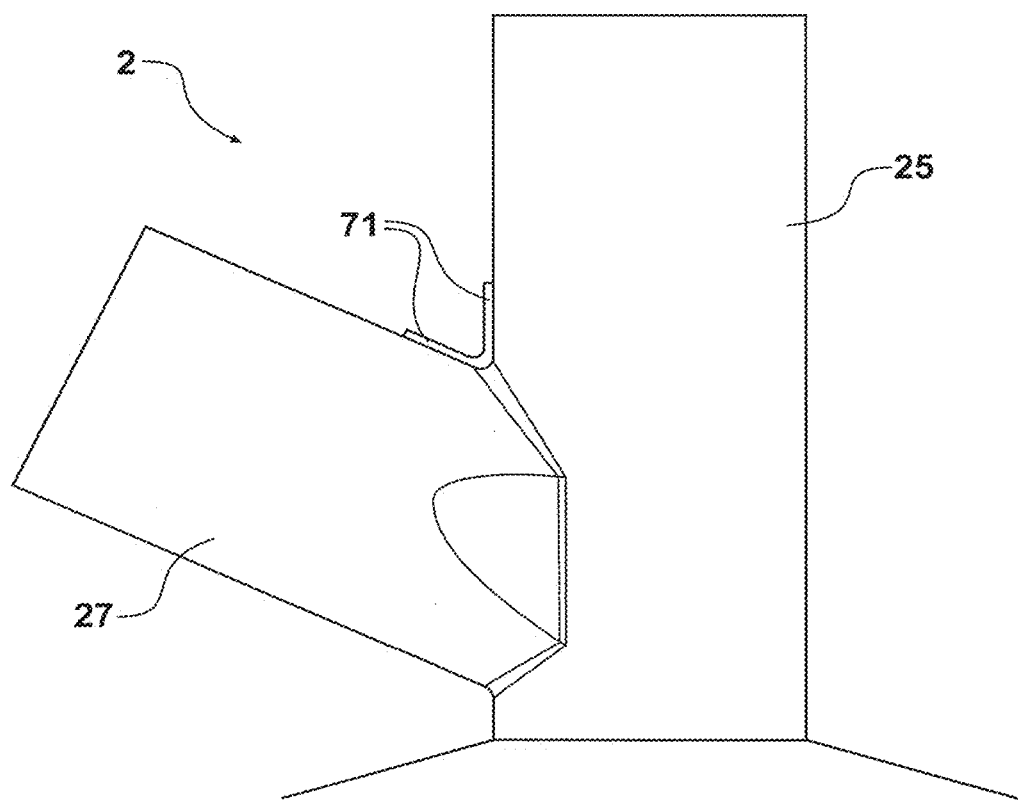
FIG. 13 is an enlarged side view of part of the closure of the trap of FIGS. 1 to 12.

Additionally, and with reference to FIG. 13, the fluid trap 1 includes alterations to prior art designs to allow the use of two or three part moulds during manufacture by replacing the typical taper stops with raised ridge stops 71 that run parallel to the respiratory circuit connection sites at the upper end of the first tube 25 and second tubes 27. This removes an overhang from the inlet assembly 2, additionally allowing the use of simpler moulding systems.

Alternative Embodiments

As an alternative to the above described fluid trap 1, the valve 7 may include a flat body having a substantially circular shape when viewed in plan. The body may be formed from a rigid material such as a rigid plastic or a rigid silicone material. The material is a suitable material that can be reprocessed, including by autoclaving or gas sterilizing.

The rigid body may comprise one or more a-rings disposed on the body that seal between the closure 5 and container 3. Further the valve 7 may comprise a biasing device or mechanism such as a spring that is positioned on the valve stem 35 of the valve 7. The spring is configured to provide a biasing force to the valve disc 37 to close the valve disc 37 when the closure 5 and the container 3 are disconnected. The spring causes the valve disc 37 to sit against the valve seat 24. When the closure 5 and container 3 are closed/engaged, the spring is stretched between the valve disc 37 and valve seat 24. The spring can be attached to the valve seat 24 and is at rest position when the valve disc 37 is located on the valve seat 24, that is, when the closure 5 and container 3 are unattached. The stretching of the spring away from its rest position, as the valve disc 37 is pushed upward, causes a biasing force to pull the valve disc 37 toward the valve seat 24. The spring can be any suitable type of spring, such as a coil spring or a leaf spring or a disc spring, for example.

In an alternative embodiment, the spring may be coupled to the valve body. The spring may be any suitable type of spring, such as a disc spring or leaf spring or coil spring, for example. The spring may be metallic. The spring may be connected to a portion of the closure 5, for example to a lower portion of the first tube 25 or to the valve seat 24 or to the valve body. The spring is preferably configured to compress when the closure 5 and container 3 are engaged with each other and pushed into a closed position. The compression of the spring will cause the valve stem 35 to be pushed upward causing the valve disc 37 to be pushed upward away from the valve seat 24. The spring places a bias force on the valve stem 35 to pull the valve disc 37 downward toward the valve seat 24. When the closure 5 and container 3 are disengaged from each other the spring relaxes, causing the valve disc 37 to be pulled onto the valve seat 24 thereby sealing off the fluid passage.

In a further alternative, the body of the valve 7 may include a second biasing device or mechanism, such as a spring, located on the underside of the valve, and may be coupled to the valve stem. The spring may be configured to be compressed as the closure 5 and container 3 are closed causing a biasing force to push outward and push the valve body downward. This downward bias force may help in creating a seal between the closure 5 and container 3. The first and second spring work in conjunction to bias the valve disc toward the valve seat. The first spring preferably has a higher spring constant than the first spring to allow the valve disc 37 to be pushed toward the valve seat 24. The springs may be any suitable type of spring, for example, coil springs or leaf springs or disc springs.

Further Embodiments

Modifications to the above described fluid trap 1 are within the scope of this disclosure. Some example modifications are described below. Like features have been given like references. Any one or more features of one embodiment may be combined with any one or more features of any other embodiment.

Figure 24:
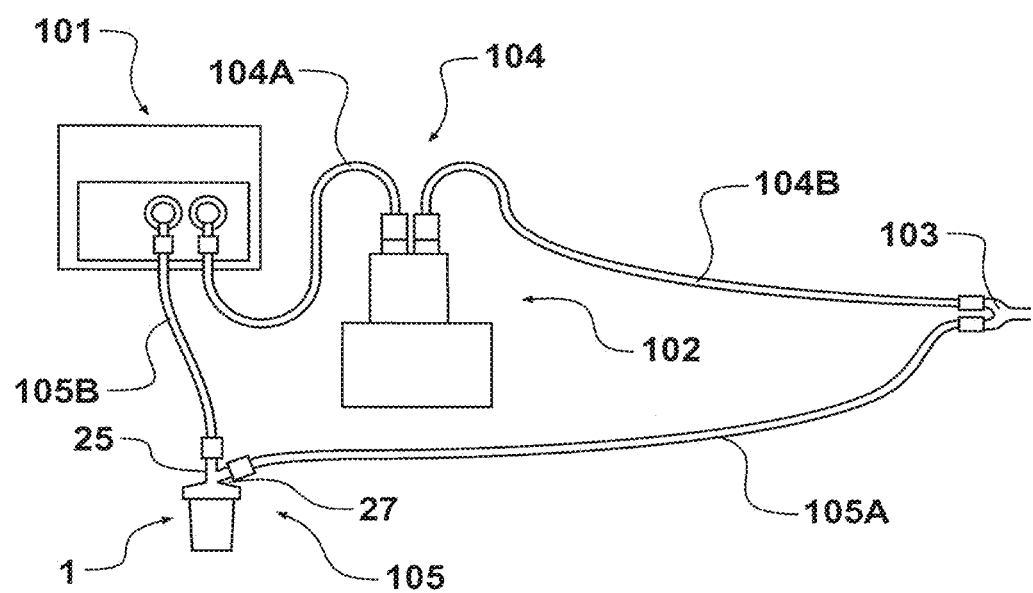
FIG. 24 is a schematic diagram of a respiratory therapy system in accordance with the present disclosure.

FIG. 24 shows an embodiment of a respiratory therapy system including the fluid trap 1. The system includes an inspiratory flow path 104 along which breathing gas is delivered from gases outlet of a ventilator 101 to a patient (not shown), and an expiratory flow path 105 along which expiratory gas flows from the patient. In the inspiratory flow path 104, a first inspiratory conduit 104a connects the ventilator 101 to an inlet of a humidifier 102. The first inspiratory conduit 104a is sometimes called a dry line. A second inspiratory conduit 104b connects an outlet of the humidifier 102 with an inlet of a wye piece 103. The second inspiratory conduit 104b may include means for heating the gas flow therein, and/or include insulation to minimize the temperature drop of the gas flow. The wye piece 103 is connectable to a patient interface (not shown). In the expiratory flow path 105, a first expiratory conduit 105a connects the wye piece 103 with the second tube 27 of the fluid trap 1. A second expiratory conduit 105b connects the first tube 25 of the fluid trap 1 with the expiratory gases inlet of the ventilator 101.

Whilst the description of the foregoing embodiments described above relate to a respiratory system in which there is a single fluid trap, respiratory therapy systems and circuits are envisioned which comprise multiple fluid traps. In one embodiment there is provided a respiratory therapy system including a dual water trap system wherein a first water trap is positioned along the expiratory flow path, and a second water trap is positioned along an inspiratory limb and/or at a catheter mount of a breathing limb of the system.

Figure 14:
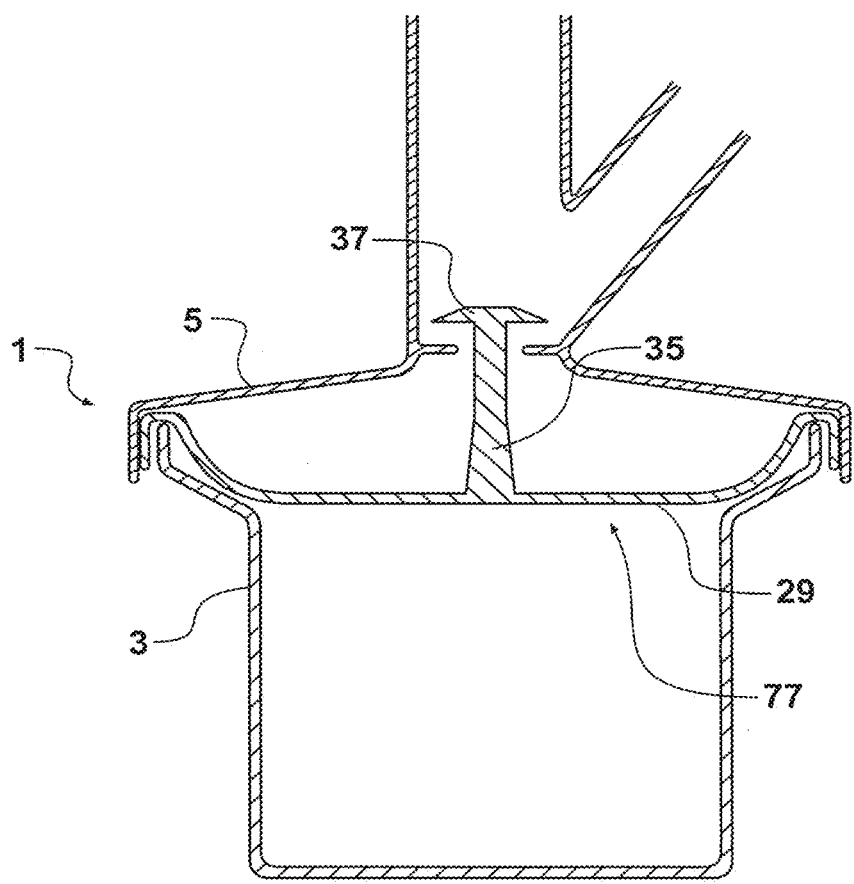
FIG. 14 is a sectional view of n alternative embodiment of a valve of a fluid trap in accordance with the present disclosure.

With reference to FIG. 14, the fluid trap 1 is provided with a revised valve 77 having similar features to valve 7. The valve 77 in this example is also a mushroom valve but valve base 29 is substantially planar across the diameter of the valve 77. The underside of the valve base 29 does not comprise the downwardly directed hollow boss 39 in this example. Valve 77 may perform adequately in achieving one or more of the advantages of the fluid trap 1. When fully assembled, the valve base 29 may remain substantially planar across the diameter, or it may bow upward towards the valve seat, depending on the stiffness of the valve base 29.

Figure 15A:
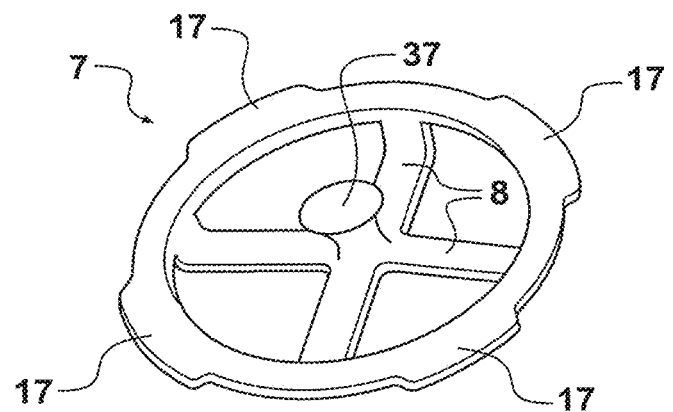
FIGS. 15a-c are perspective views of further alternative valve embodiments.
Figure 15B:
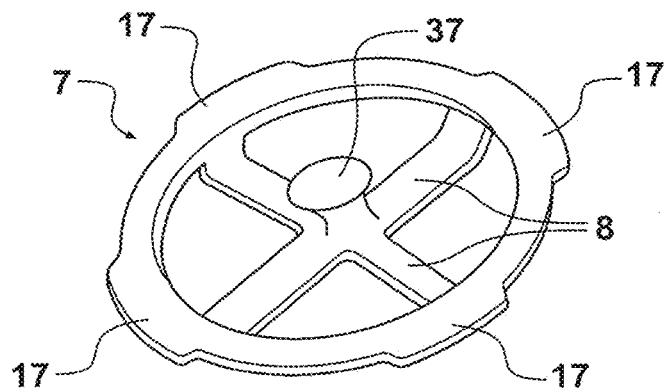
Figure 15C:
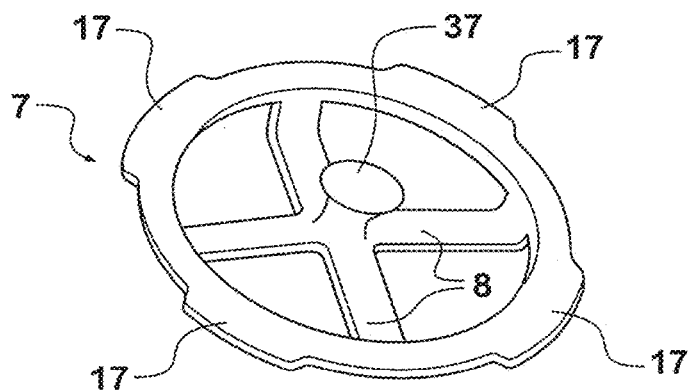

With reference to FIG. 15, three example valves 7 are shown, manufactured so as to have different properties. Example a) is cast from silicone having a Shore hardness of 37A. Example b) is cast from silicone having a Shore hardness of 40A. Example c) is moulded from silicone having a Shore hardness of 40A. In these examples the valves 7 comprise a four spoke design having four equispaced spokes 8 linking the valve stem 35 to the valve outer wall 31. Each of these examples is provided with four equispaced flanges 17. The valve may have a Shore hardness in the range of 5A-95A, 10A-90A, 20A-60A, 30A-50A, 35A-45A, and or any other suitable range.

Figure 16:
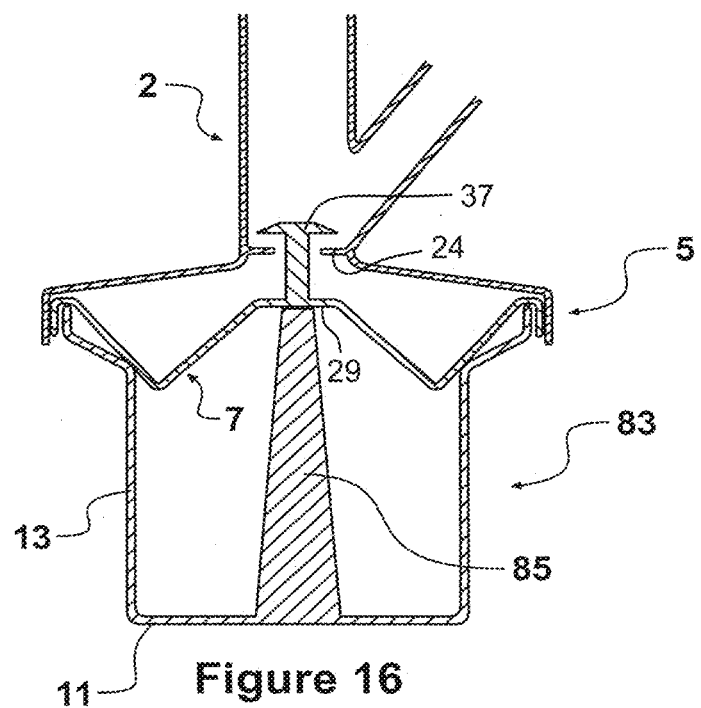
FIG. 16 is a sectional perspective view of an alternative water trap in accordance with the present disclosure.
Figure 17:
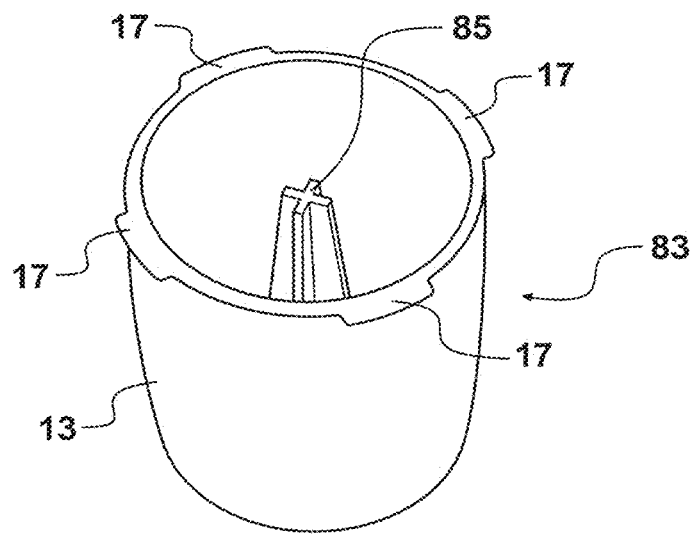
FIG. 17 is a perspective view front above of a container of trap of FIG. 6.
Figure 18A:
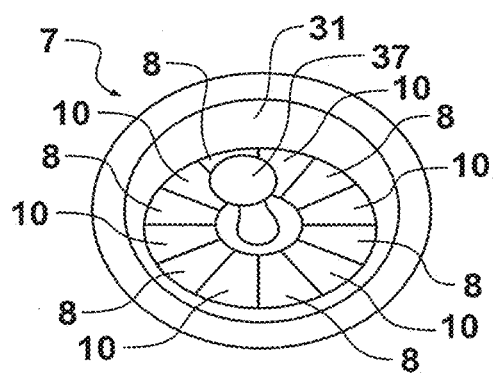
FIGS. 18a-d are perspective views of further alternative valve embodiments.
Figure 18B:
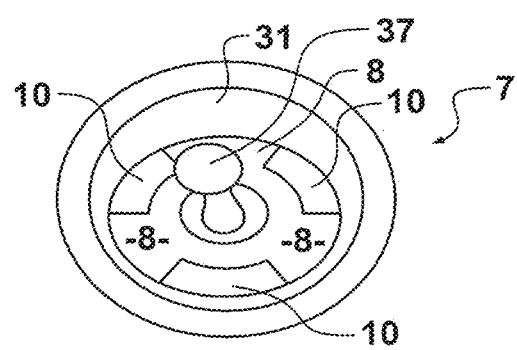
Figure 18C:
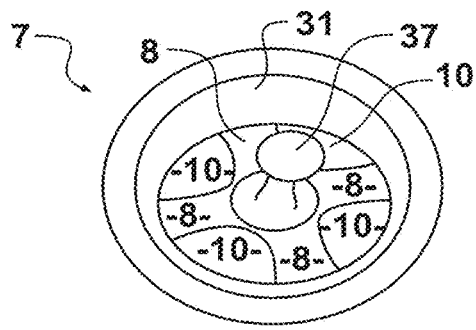
Figure 18D:
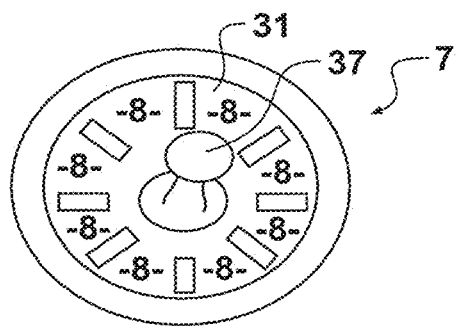

With reference to FIGS. 16 and 17, a further embodiment of water trap 1 comprises a first modified container 83 having similar features to container 3 described above. In this example, first modified container 83 is provided with a central stem 85 (e.g., a pusher 85, a projection 85, an actuator 85) which projects upwardly from container base 11 such that the tip of stem 85 engages the central region of valve base 29 of valve 7. As the container 3 and closure 5 are assembled, the stem 85 engages and pushes the centre of the underside of the valve 7, pushing the valve upwardly during assembly such that the valve disc 37 pushes through valve seat 24 correctly during assembly. Stem 85 provides a robust structure for ensuring the valve stem and valve disc 37 are in the correct position once the container 3 and closure 5 are fully assembled.

With reference to FIG. 18 various alternative structures of valve 7 are provided. Each valve 7 comprises a valve base 29 having a plurality of spokes 8 extending radially outwardly from the valve stem 35 to valve outer wall 31. The example of FIG. 18 a) comprises six spokes. FIG. 18 b) three spokes, FIG. 18 c) four spokes, and FIG. 18 d) eight spokes. In each example the diameter of the central region of the valve base 29 of each valve 7 varies with the example of FIG. 18 a) having a relatively small diameter central region and FIG. 18 d) having a relatively large diameter central region. In the example of FIG. 18 d), the spokes 8 are structured such that there are relatively small slots 10 defined between each spoke 8. "Slots 10" may also be referred to herein as "recesses 10" and/or "cut-outs 10". In these examples the size of the slots or cut-outs or recesses 10 may be relatively large, such as in the example of FIG. 18 b) for example. The number, size and shape of the spokes 8 can be selected to provide the desired flexibility, deformation, and movement between different parts of the valve 7, and in particular between the valve stem 35 relative to the valve outer wall 31. The number, size and shape of spokes 8 can be selected to optimise assembly, lift and spring back force.

Figure 19:
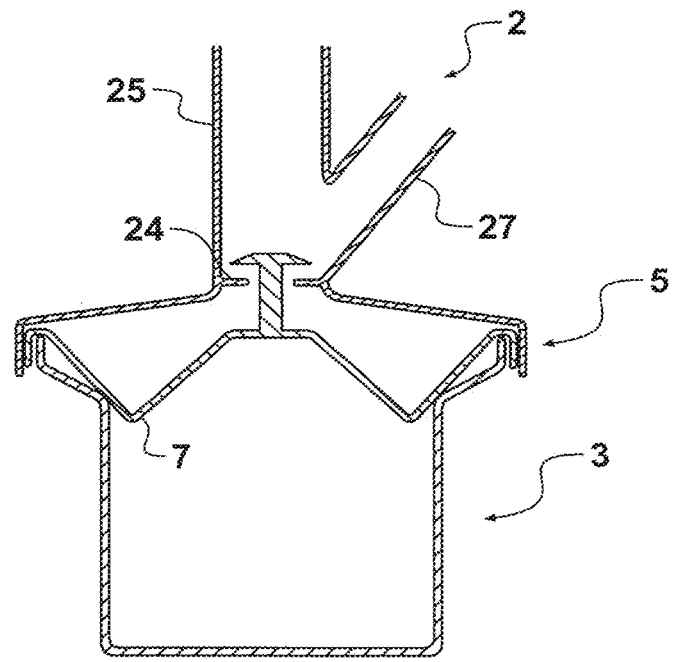
FIG. 19 is a sectional side view of another alternative water trap in accordance with the present disclosure.
Figure 20:
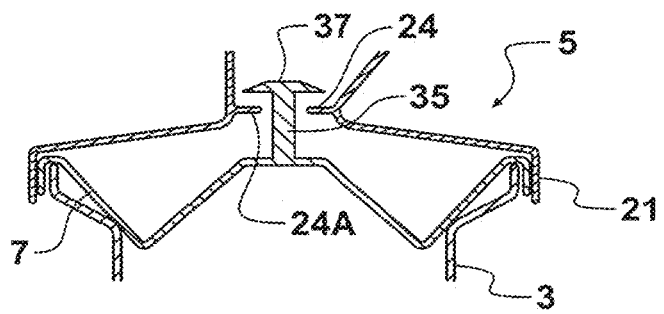
FIG. 20 is an enlarged sectional side view of part of the trap of FIG. 19.
Figure 21:
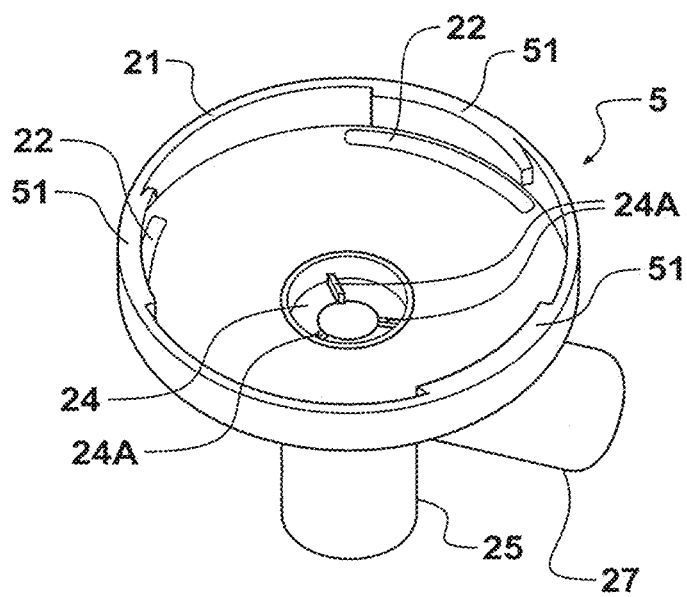
FIG. 21 is a perspective view from below of a closure of the trap of FIGS. 19 and 20.

With reference to FIGS. 19 to 21, another modified fluid trap 1 is shown in which the interference between the soft seal spring mechanism of the valve 7 and the container 3 is altered such that the lift of the valve stein 35 and valve disc 37 is increased. In this embodiment, the valve disc 37 pushes through the hole in the valve seat 24 during the assembly of the container 3 to the closure 5. However, the container 3 volume decreases. In one example, the container volume may decrease to approximately 100 ml, which is still within the preferred volume range desirable for the fluid trap 1.

In order to make it easier for the valve disc 37 to push through the hole in the valve seat 24, flex points have been added in the form of radially outwardly extending ribs 24A on the underside of the valve seat 24. These flex points reduce the force required to push the valve disc 37 through the hole during the assembly process.

Figure 22:
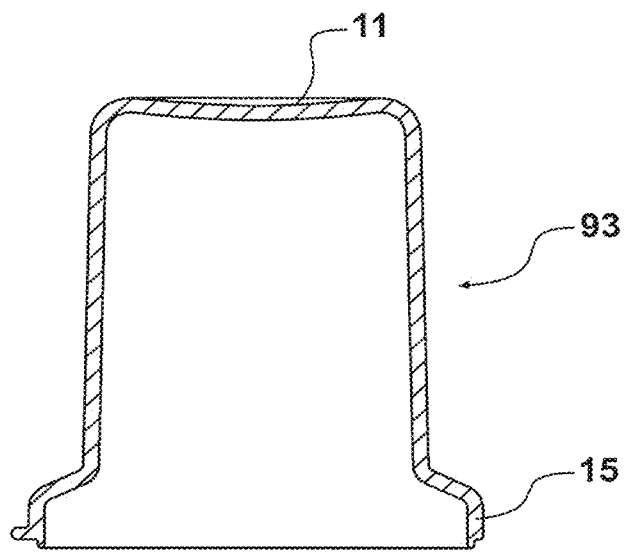
FIG. 22 is a sectional side view of a container of another alternative fluid trap in accordance with the present disclosure.
Figure 23:
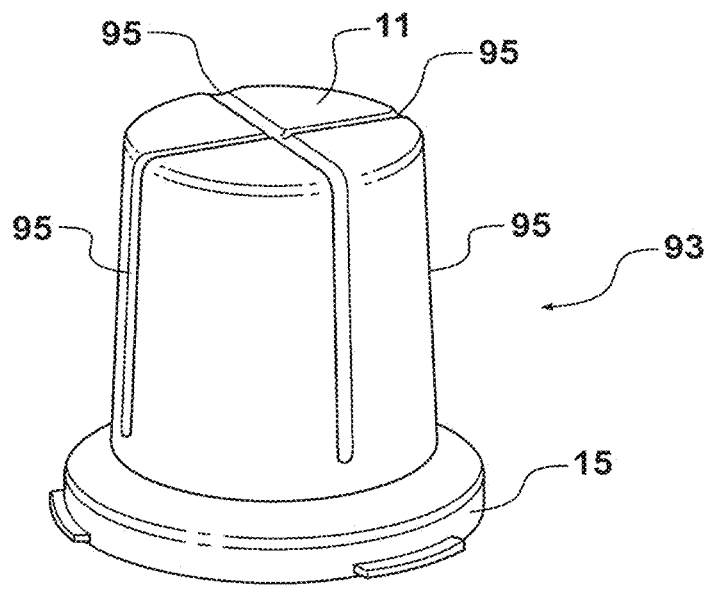
FIG. 23 is a perspective view of the container of FIG. 22.

With reference to FIGS. 22 and 23, a further modified rescuable fluid trap 1 comprises a second modified container 93 provided with external drain channels 95 which extend from the container base 11 and along the sides of the second modified container 93. Whilst any suitable number of drain channels can be provided, in this example, four equispaced drain channels 95 are provided.

The container 3 is typically cleaned using washer disinfectors and is placed inside a cleaning receptacle or chamber with the container mouth 15 facing down. A small amount of water can be collected on the base 11 of the container 3 due to its' geometry (the base 11 of the container 3 is intentionally not flat in order to avoid an unstable container 3 when placed on a flat surface due to warping and the sprue area). Drain channels 95 can help to stop this from occurring.

Further Possible Benefits

A water trap 1 in accordance with aspects of this disclosure may provide one or more of the following benefits or advantages:

Clean-ability: The water trap 1 can be relatively easily dis-assembled, and can help satisfy cleaning requirements that may be specified by law or by policy document or by a regulatory standard. The components of the water trap 1 can also be cleaned without being damaged due to cleaning methods and handling. The materials of the water trap also are robust such that the water trap does not get damaged during cleaning.

The container 3 can be relatively easily dis-assembled to empty out condensate without spillage or contamination to the nurse, for example. When the container 3 is dis-assembled, there should be no ventilator leak alarms. Once the container 3 is emptied, it is relatively easy to reassemble, with the trap 1 remaining in its current, in use, position.

Relatively large container volume: the larger the container 3 volume, the less number of times the nurse needs to empty the container 3. However, the container volume should not increase so much as to affect the compressible volume of the circuit. This factor may be particularly applicable where the trap 1 is used with the expiratory limb of the system.

Connections: in at least some examples, medical grade taper connections will be used for connecting to all external components.

Resistance to flow should ideally be no worse than a single use, prior art, trap.

Unless the context clearly requires otherwise, throughout the description, the words "comprise", "comprising", and the like, are to be construed in an inclusive sense as opposed to an exclusive or exhaustive sense, that is to say, in the sense of "including, but not limited to".

Although this invention has been described by way of example and with reference to possible embodiments thereof, it is to be understood that modifications or improvements may be made thereto without departing from the scope of the invention. The invention may also be said broadly to consist in the parts, elements and features referred to or indicated in the specification of the application, individually or collectively, in any or all combinations of two or more of said parts, elements or features. Furthermore, where reference has been made to specific components or integers of the invention having known equivalents, then such equivalents are herein incorporated as if individually set forth.

Any discussion of the prior art throughout the specification should in no way be considered as an admission that such prior art is widely known or forms part of common general knowledge in the field.

The invention claimed is:

1. A fluid trap for a breathing limb of a respiratory therapy system, comprising:
   a. at least one inlet configured to be connected to the breathing limb to receive fluid from the breathing limb;
   b. a container configured to collect fluid received from the at least one inlet;
   c. a closure comprising the at least one inlet, the closure and container being configured to be removeably mounted together to close the container; and
   d. a valve comprising a central valve stem and a base portion, the central valve stem comprising a valve seal, the base portion comprising an inclined surface and a plurality of cut-outs, the base portion configured to engage the container when the closure and container are mounted together, the valve configured to be removeably mounted on at least one of the container and the closure, and configured to be in a closed condition which prevents fluid from the at least one inlet flowing through the valve when the closure is not mounted on the container, the valve being further configured to be in an open condition which allows fluid from the at least one inlet into the container when the closure is mounted on the container and the valve engages the container, wherein the valve is formed as a unitary member from a resiliently deformable material such that resilient deformation of the base portion creates a biasing force, to form a seal between the valve seal and the at least one inlet when the valve is in the closed condition.

2. The fluid trap of claim 1 wherein resilient deformation of the valve moves the valve from the closed condition to the open condition, when the container and the closure are mounted together.

3. The fluid trap of claim 1 wherein the valve is configured to be mounted on one of the container and the closure so as to be located between the closure and the container when the closure and the container are mounted together.

4. The fluid trap of claim 1 wherein the valve comprises, in transverse cross section, at least one lower projection which engages the container, at least one upper projection that engages the closure, relative axial movement between the closure and container causing relative movement between the at least one upper projection and the at least one lower projection which moves the valve between the open condition and the closed condition.

5. The fluid trap of claim 4 wherein the valve comprises a substantially 'W' shaped transverse cross section having, in transverse cross section, a pair of upper projections and a pair of lower projections.

6. The fluid trap of claim 1 wherein the plurality of cut-outs are configured to reduce a weight and/or to improve a flexibility of the valve.

7. The fluid trap of claim 1 wherein the closure, the container and the valve are configured such that the container and the closure cannot be mounted together unless the valve is present.

8. The fluid trap of claim 1 wherein the valve is configured to provide at least:
   a first function of providing a valve that opens or closes the at least one inlet; and
   a second function of providing a fluid seal between the container and the closure.

9. The fluid trap of claim 1 wherein the container and the closure are configured to be mounted together using a push-rotate fit in which the closure and the container are pushed together in a direction along a longitudinal axis of the container/closure, and simultaneously rotated relative to one another about the longitudinal axis of the container/closure.

10. The fluid trap of claim 1 wherein at least one of the container and the closure comprise a guiding formation configured to guide the other of the container and the closure as the container and the closure are pushed and rotated together.

11. The fluid trap of claim 10 wherein at least one of the container and the closure comprises one or more flanges that protrude outwardly from the container or the closure, each flange of the one or more flanges being configured to engage with the guiding formation and move along the guiding formation as the container and the closure are urged together into the closed condition.

12. The fluid trap of claim 1 further comprising a security formation configured to provide at least one of an audible and a tactile confirmation when the container and the closure are fully mounted together.

13. The fluid trap of claim 1 wherein one of the container and the closure comprises a peripheral lip configured to be positioned adjacent a longitudinally extending peripheral skirt provided on the other of the container and the closure, the peripheral lip comprising at least one radially directed flange portion configured to be received in a corresponding recessed portion of the peripheral skirt, relative rotation between the container and the closure causing the flange portion to overlap with a non-recessed portion of the peripheral skirt, the overlap resisting removal of the closure from the container in a longitudinal direction.

14. The fluid trap of claim 1 wherein the valve comprises a plurality of radially extending spokes extending between a peripheral side wall of the valve and the central valve stem, a cut-out of the plurality of cut-outs being defined between each pair of adjacent spokes.

15. The fluid trap of claim 1 wherein the container comprises at least one drain channel extending along an exterior of the container from a base of the container.

16. The fluid trap of claim 1, wherein the at least one inlet includes a valve seat surrounding an aperture, the central valve stem extending through the aperture, wherein the valve seal seals against the valve seat in the closed condition.

17. The fluid trap of claim 16, wherein the valve seal is deformed to pass through the aperture on assembly of the fluid trap.

18. A respiratory therapy system comprising the fluid trap of claim 1.

19. A circuit kit for use with a respiratory therapy system comprising the fluid trap of claim 1 and any one or more of:
  a. a breathing limb comprising an inspiratory circuit;
  b. a breathing limb comprising an expiratory circuit that may be breathable or not;
  c. a breathing limb comprising a catheter mount;
  d. one or more connectors or adapters;
  e. a humidifier chamber;
  f. a wye piece; and
  g. a pressure relief valve.

* * * * *

UNITED STATES PATENT AND TRADEMARK OFFICE
CERTIFICATE OF CORRECTION

Page 1 of 2

PATENT NO. : 11,724,058 B2
APPLICATION NO. : 16/487343
DATED : August 15, 2023
INVENTOR(S) : Nathan Lee Gray It is certified that error appears in the above-identified patent and that said Letters Patent is hereby corrected as shown below:

On the Title Page

Column 2, Line 2, under item (57) Abstract, delete "d" and insert --and in--.

In the Specification

In Column 1, Line 15, delete "pail" and insert --part--.

In Column 2, Line 43, delete "pails" and insert --parts--.

In Column 7, Lines 43-44, delete "a of" and insert --part of--.

In Column 7, Line 51, delete "n" and insert --an--.

In Column 7, Line 58, delete "front" and insert --from--.

In Column 7, Line 59, delete "of" and insert --of the--.

In Column 7, Line 59, delete "6;" and insert --16;--.

In Column 7, Line 67, delete "20:" and insert --20;--.

In Column 9, Line 4, delete "tubes" and insert --tube--.

In Column 9, Line 54, delete "form" and insert --form of--.

In Column 10, Line 16, delete "pan" and insert --part--.

In Column 10, Line 36, delete "that that" and insert --that--.

Signed and Sealed this
Thirty-first Day of October, 2023

Katherine Kelly Vidal
*Director of the United States Patent and Trademark Office*

CERTIFICATE OF CORRECTION (continued)
U.S. Pat. No. 11,724,058 B2

In Column 10, Lines 46-47, delete "a valve" and insert --valve--.

In Column 14, Line 37, delete "a-rings" and insert --o-rings--.

In Column 14, Line 38, delete "a-ring" and insert --o-ring--.

In Column 14, Line 40, delete "a-ring" and insert --o-ring--.

In Column 14, Line 41, delete "a-ring" and insert --o-ring--.

In Column 14, Line 48, delete "a-rings" and insert --o-rings--.

In Column 14, Line 49, delete "a-ring" and insert --o-ring--.

In Column 14, Line 50, delete "a-ring" and insert --o-ring--.

In Column 14, Line 52, delete "a-ring" and insert --o-ring--.

In Column 14, Line 53, delete "a-ring" and insert --o-ring--.

In Column 14, Line 55, delete "a-ring" and insert --o-ring--.

In Column 14, Line 55, delete "a-ring" and insert --o-ring--.

In Column 16, Line 23, delete "Obvious" and insert --obvious--.

In Column 18, Line 15, delete "tubes" and insert --tube--.

In Column 18, Line 27, delete "a-rings" and insert --o-rings--.

In Column 20, Line 4, delete "and or" and insert --and/or--.

In Column 20, Line 46, delete "stein" and insert --stem--.

In Column 21, Line 20, delete "The" and insert --In Use: the--.

In Column 21, Line 38, delete "trap." and insert --water trap.--.

In the Claims

In Column 22, Claim 1, Line 22, delete "force," and insert --force--.